(12) United States Patent
Coria et al.

(10) Patent No.: US 9,511,137 B2
(45) Date of Patent: Dec. 6, 2016

(54) ADJUVANT FOR VACCINES, VACCINES THAT COMPRISE SAID ADJUVANT AND USES THEREOF

(75) Inventors: Mirta L. Coria, Buenos Aires (AR); Karina A. Pasquevich, Buenos Aires (AR); Andres E. Ibanez, Buenos Aires (AR); Guillermo H. Giambartolomei, Buenos Aires (AR); Juliana Cassataro, Buenos Aires (AR); Maria Victoria Delpino, Buenos Aires (AR)

(73) Assignees: CONSEJO NACIONAL DE INVESTIGACIONES CIENTIFICAS Y TECNICAS, Cuidad Autonoma de Buenos Aires (AR); INIS BIOTECH LLC, Milford Kent Country, DE (US)

( * ) Notice: Subject to any disclaimer, the term of this patent is extended or adjusted under 35 U.S.C. 154(b) by 98 days.

(21) Appl. No.: 13/502,721

(22) PCT Filed: Oct. 18, 2010

(86) PCT No.: PCT/ES2010/070667
§ 371 (c)(1),
(2), (4) Date: Jun. 29, 2012

(87) PCT Pub. No.: WO2011/048248
PCT Pub. Date: Apr. 28, 2011

(65) Prior Publication Data
US 2012/0258145 A1    Oct. 11, 2012

(30) Foreign Application Priority Data

Oct. 19, 2009  (AR) ............................ P20090104015

(51) Int. Cl.
| | |
|---|---|
| *A61K 39/39* | (2006.01) |
| *C12N 5/10* | (2006.01) |
| *C12N 15/85* | (2006.01) |
| *C07K 14/23* | (2006.01) |
| *A61P 37/04* | (2006.01) |
| *A61K 39/00* | (2006.01) |

(52) U.S. Cl.
CPC ............... *A61K 39/39* (2013.01); *C07K 14/23* (2013.01); *A61K 2039/542* (2013.01); *A61K 2039/55516* (2013.01)

(58) Field of Classification Search
None
See application file for complete search history.

(56) References Cited

FOREIGN PATENT DOCUMENTS

ES    2190350    7/2003

OTHER PUBLICATIONS

Bowie et al (Science, 1990, 257:1306-1310).*
Burgess et al (J. of Cell Bio. 111:2129-2138, 1990).*
Lazar et al. (Molecular and Cellular Biology, 1988, 8:1247-1252).*
Bork (Genome Research, 2000,10:398-400).*
Coria et al. (Abstract 028, SAIC LIV Annual Scientific Meeting, p. 59).*
Dvorak et al. (Immunology vol. 27, pp. 99-114).*
Giambartolomei, G. H., Zwerdling A., Cassataro, J., Bruno, L., Fossati, C.A., and Philipp, M.T., "Lipoproteins, Not Lipopolysaccharide, Are the Key Mediators of the Proinflammatory Response Elicited by Heat-Killed *Brucella abortus*." The Journal of Immunology, 2004, 173: 4635-4642.
Murillo M., Grillo, M.J., Rene, J., Marin, C.M., Barberan, M., Goni, M.M., Blasco, J.M., Irache, J.M., Gamazo C., "A *Brucella ovis* antigenic complex bearing poly-ϵ-caprolactone microparticles confer protein against experimental brucellosis in mice." Vaccine 19 (2001) 4099-4106.
Pasquevich, K.A., Estein, S.M., Samartino, C.G., Zwerdling, A., Coria, L.M., Barionuevo, P., Fossati, C.A., Giambartolomei, G.H., Cassataro, J., "Immunization with Recombinant *Brucella* Species Outer Membrane Protein Omp16 or Omp19 in Adjuvant Induces Specific CD4+and CD8+ TCells as Well as Systemic and Oral Protection against *Brucella abortus* Infection," Infection and Immunity, Jan 2009, p. 436-445.
Gil, F. S., Turner, B., Walker, M.J, Djordjevic, S.P., Chin, J.C., "Contribution of adjuvant to adaptive immune responses in mice against *Actinobacillus pleuropneumoniae*," Microbiology (1999),145, 2595-2603.

* cited by examiner

*Primary Examiner* — Robert A Zeman
(74) *Attorney, Agent, or Firm* — Muncy, Geissler, Olds & Lowe, P.C.

(57) ABSTRACT

Adjuvant for vaccines that comprises a non-lipidated bacterial outer-membrane polypeptide (Omp), in which the bacteria may be of those of *Brucella* genus. The adjuvant may be a modified polypeptide or may be, for example, the Omp19S polypeptide or the Omp16S polypeptide, parts or mixtures of the two. In a preferred embodiment, the adjuvant is the non-lipidated polypeptide included in SEQ ID No: 1, or parts thereof. In a further preferred embodiment, the adjuvant is the non-lipidated polypeptide included in SEQ ID No: 2 or parts thereof.

3 Claims, 21 Drawing Sheets

ADJUVANT FOR VACCINES, VACCINES THAT COMPRISE SAID ADJUVANT AND USES THEREOF

The present application refers to an adjuvant for vaccines that comprises a non-lipidated bacterial outer-membrane polypeptide (Omp), wherein the bacteria may be of the *Brucella* genus. The adjuvant may be a modified polypeptide; it may be, for example, the Omp19S polypeptide or parts thereof, the Omp16S polypeptide or parts thereof, or mixtures of both. In a preferred embodiment, the adjuvant is the non-lipidated polypeptide comprised in SEQ ID No: 1 or parts thereof. In another preferred embodiment, the adjuvant is the non-lipidated polypeptide comprised in SEQ ID No: 2 or parts thereof.

BACKGROUND

Immunological adjuvants are substances that, incorporated to the antigen (Ag) or simultaneously administered with it, induce a more effective immune response against the antigen. They may be used to enhance the immune response against an Ag in several ways: they can enhance the magnitude of the immune response against a weak Ag; increase the rate and duration of the immune response, modulate antibody (Ab) avidity; isotypes or subclass distribution; stimulate and modulate the cellular immune response; promote the induction of local immune response (e.g., mucosa); decrease the amount of necessary Ag and reduce the vaccine cost; or they may help in avoiding Ag competence which exists in combined vaccines (Singh and O'Hagan. Advances in vaccine adjuvants. Nat Biotechnol. 17 (11):1075-81. 1999).

Throughout vaccine history, and ever since the complete Freund adjuvant (CFA) based on a mycobacterial emulsion with water and oil, many preparations have been tested with higher or lower success. The most used and allowed adjuvant for human use is aluminum, as hydroxide or phosphate salts. Other adjuvants consist of bacterial components such as endotoxins, particles such as liposomes, oil emulsions such as saponins, and other different molecules (Petrovsky and Aguilar. Vaccine adjuvants: current state and future trends. Immunol Cell Biol. 82 (5):488-96. 2004). Most of the historically used adjuvants, such as aluminum salts, preferably stimulate the T helper (Th) type 2 immune response (Liljeqvist and Stahl. Production of recombinant subunit vaccines: protein immunogens, live delivery systems and nucleic acid vaccines. J Biotechnol. 73 (1):1-33. 1999), increasing the production of Abs. However, there are other vaccines, such as BCG vaccine and adjuvants incorporating oil compounds, which stimulate the Th1 immune response (Victoratos, Yiangou, Avramidis and Hadjipetrou. Regulation of cytokine gene expression by adjuvants in vivo. Clin Exp Immunol. 109 (3):569-78. 1997). The choice of the adjuvant for a vaccine should be carefully selected in the future, not just as a function of the amount of response, but also on the quality of the elicited response. On the other hand, the traditionally used vaccination methodology (intramuscular or intradermic vaccine in aluminum hydroxide) has been useful for inducing systemic humoral immune responses but generally fail to induce cellular and local immune responses, such as in mucosa (Moyle, McGeary, Blanchfield and Toth. Mucosal immunization: adjuvants and delivery systems. Curr Drug Deliv. 1 (4):385-96. 2004). There is a greater need in the design of vaccines capable of inducing strong cellular Th1 type and cytotoxic T cell (TCL) immune responses which may prevent viral chronic infections, infections related to intracellular pathogens or cancer (therapeutical vaccines) (Seder and Hill. Vaccines against intracellular infections requiring cellular immunity. Nature. 406 6797):793-8. 2000).

Other important considerations, (besides promoting a specific and efficient immune response against the antigen) are related to those important features for the substance to be used in clinical practice. Optimal formulations must be safe, stable, biodegradable, inert and of low manufacturing cost. The list of substances complying with all these requirements is quite short, up to now, the adjuvants approved for use in humans are restricted to aluminum salts, MF59 (an oil in water emulsion), MLP (monophosphoryl-glycolipid), viral particles (HBV and HPV), IRIV (proteoliposome composed of phospholipids, influenza virus hemagglutinin and a determined target antigen); and the B subunit of the cholera toxin (Reed, Bertholet, Coler and Friede. New horizons in adjuvants for vaccine development. Trends Immunol. 30 (1):23-32. 2009). Adjuvants must not induce adverse reactions when used in prophylactic vaccines, although certain reactions are accepted in therapeutic vaccines. In the veterinary health field, efficacy is an element of great importance and certain levels of side effects are tolerated (Sesardic. Regulatory considerations on new adjuvants and delivery systems. Vaccine. 24 Suppl 2 S2-86-7. 2006).

Given that the main entry for the majority of infections are mucosal surfaces, the ability to generate mucosal immunity after administration of an Ag could provide for an early defense against these pathogens. Unfortunately, after administration of Ags by the oral route, there is degradation in the gastrointestinal tract, little absorption and low long-term efficacy, therefore repeated administrations and large amounts of Ag are needed for stimulating and maintaining the immune response. In addition, it has been observed immunological tolerance to those soluble Ags administered through the oral route (Moyle et al. Mucosal immunization: adjuvants and delivery systems. Curr Drug Deliv. 1 (4):385-96. 2004). Oral adjuvants used up to now, such as cholera toxin (TC), for instance, show serious risks after administration (Fujihashi, Koga, van Ginkel, Hagiwara and McGhee. A dilemma for mucosal vaccination: efficacy versus toxicity using enterotoxin-based adjuvants. Vaccine. 20 (19-20):2431-8. 2002), hence it is very important in this field to develop safer adjuvants that allow an efficient delivery of the Ags to the mucosal surfaces, with subsequent induction of immune response in the mucosa.

At the international level, the list of products with adjuvant properties is continuously larger; however, only a reduced number is used in the formulation of veterinary and human vaccines (Aucouturier, Dupuis and Ganne. Adjuvants designed for veterinary and human vaccines. Vaccine. 19 (17-19):2666-72. 2001; Petrovsky et al. Vaccine adjuvants: current state and future trends. Immunol Cell Biol. 82 (5):488-96. 2004). For that reason, it is important to develop efficient adjuvants that, at the same time, are safe for human and animal vaccines.

Nowadays, the majority of adjuvants capable of inducing strong Th1 responses are those based on oil emulsions, such as the incomplete Freund adjuvant (IFA), however, these entail adverse reactions at the site of injection, such as sterile abscesses and granulomas. In light of the foregoing, the development of parenteral and mucosal adjuvants which induce Th1 and CTL responses is highly relevant.

In the present invention, two new adjuvants are provided: Omp16S and Omp19S. These substances increase and/or modulate immune responses against co-administered Ags, favoring the development of Th1-, Th17- or CTL-type immune responses.

BRIEF SUMMARY OF THE INVENTION

An adjuvant for vaccines comprising a non-lipidated bacterial outer-membrane polypeptide (Omp), wherein the bacteria may be of the *Brucella* genus. The adjuvant may be a modified polypeptide or may be, for example, the Omp19S polypeptide or parts thereof, or the Omp16S polypeptide or parts thereof, or mixtures of both. In a preferred embodiment, the adjuvant is the non-lipidated polypeptide comprised in SEQ ID No: 1 or parts thereof. In another preferred embodiment, the adjuvant is the non-lipidated polypeptide comprised in SEQ ID No: 2 or parts thereof.

It is also provided herein a vaccine comprising the adjuvant, at least a non-lipidated bacterial outer-membrane polypeptide (Omp), and at least an antigen, wherein the bacteria may be of the *Brucella* genus and wherein said vaccine may be for mucosal or parenteral administration. The vaccine adjuvant may be a modified polypeptide or may be, for instance, the Omp19S polypeptide or parts thereof, or the Omp16S polypeptide or parts thereof, or mixtures of both. In a preferred embodiment, the adjuvant is the non-lipidated polypeptide comprised in SEQ ID No: 1 or parts thereof. In another preferred embodiment, the adjuvant is the non-lipidated polypeptide comprised in SEQ ID No: 2 or parts thereof.

The use of the adjuvant for the manufacture of a vaccine against a pathogen is provided.

The use of the adjuvant for the manufacture of an antitumor vaccine or an immunomodulating composition is provided.

Expression vectors are provided for eukaryotes, comprising the sequences SEQ ID No: 1 or SEQ ID No: 2.

Modified eukaryote cells are provided, expressing the sequences SEQ ID No: 1 or SEQ ID No: 2.

DESCRIPTION OF THE DRAWINGS

FIG. 1 shows: 15% polyacrylamide gel stained with Coomasie Blue, onto which samples of purified and lipopolysacharide(LPS)-depleted Omp19S and Omp16S were seeded. 20 μg of total protein were seeded in all lanes. Omp19S degraded with proteinase K (Omp19SPK) was also run in the same gel, and was used as a control in some experiments.

FIG. 2 shows that expression of the α4β7 protein increases in mesenteric lymph nodes from BALB/c animals immunized with Omp19S as adjuvant by the oral route. The animals were orally immunized with: (i) bovine ovalbumin (OVA), (ii) Omp19S+OVA, or (iii) choleric toxin (TC)+OVA. $2\times10^6$ mesenteric lymph node cells corresponding to each immunization group were labeled with anti-CD4 (FITC), anti-CD8 (PE-Cy5.5) and anti-α4β7 (PE) antibodies (Abs). Upper right quadrant numbers represent the frequency of $CD8^+$ (A) and $CD4^+$ (B) T cells which express the α4β7 protein. The isotype control frequency was subtracted in all cases. n/group=5. Data are representative of two independent experiments.

FIG. 3 shows that Omp19S, when administered as an oral adjuvant, induces a T cell immune response in vivo. Delayed-type hypersensitivity reaction (DTH) was determined in response to inoculation of 20 μg OVA into the footpad of animals immunized as described in FIG. 2. Bars represent the mean fold increment in the footpad skin between right and left foot±standard error of the mean (SEM) at 48 h (A) and 72 h (B), n/group=5, representing 2 experiments with similar results.

FIG. 4 shows that Omp19S, when administered as oral adjuvant, induces an increase in the proliferative capacity of splenocytes in response to antigen stimulation. The splenocytes of animals immunized as described in FIG. 2 were stimulated with either 100 μg/ml OVA or without antigen. Cells were cultured with $^3$H thymidine for 18 h and incorporated radioactivity was measured. Results are shown as stimulation index (S.I.) that represents OVA-stimulated splenocyte cpm/non-stimulated splenocyte cpm. An S.I.>2 is considered positive. Values represent the mean of determinations made by triplicate for 5 animals/group±SEM.

FIG. 5 shows that Omp19S, when administered as oral adjuvant, induces a cellular immune response with cytokine production (IFN-γ and IL-17) after antigenic stimulation. Spleen splenocytes of each group immunized as described in FIG. 2 (n/group=5) were stimulated in vitro with different concentrations of OVA (100 μg/ml and 1000 μg/ml) or complete medium (RPMI). The culture supernatants were harvested 72 h after stimulation. Cytokine concentrations (A) interferon (IFN-γ), (B) IL-4, (C) IL-2, (D) IL-10 and (E) IL-17 (pg/ml) in the culture supernatants were determined by ELISA. Values represent the mean of determinations made by duplicate for each mouse±SEM, representing 2 experiments with similar results.

FIG. 6 shows that Omp19S, when administered as oral adjuvant, stimulates the induction of $CD4^+$ and $CD8^+$ specific T cells which produce IFN-γ. Splenocytes of animals immunized by the oral route with (i) OVA, (ii) Omp19S+OVA or (iii) TC+OVA, were stimulated either with $OVA_{323}$+A20J+OVA 500 μg/ml or with complete culture medium (no stimulation) for 18 h and with Brefeldin A for the last 4 h of culture. Then, cells were stained with specific anti-CD4 (PE/Cy5) and anti-CD8 (Alexa Fluor 647) Abs and subsequently fixed, permeabilized and incubated with an anti-IFN-γ (PE) Ab or isotype control Ab (PE). Numbers in the upper right quadrant represent the frequency of $CD4^+$ (A) or $CD8^+$ (B) T cells expressing IFN-γ. The isotype control frequency and the production of IFN-γ by unstimulated cells of the same group were subtracted in all cases. This way, the indicated percentage corresponds to the production of OVA specific IFN-γ. Data are representative of two independent experiments.

FIG. 7 shows that expression of the α4β7 protein increases on T cells of mesenteric lymph nodes from BALB/c animals orally immunized with Omp16S as adjuvant. Groups of animals were immunized by the oral route with: (i) OVA, (ii) Omp16S+OVA, or (iii) TC+OVA. $2\times10^6$ mesenteric lymph node cells corresponding to each group were marked with anti-CD8 (PE-Cy5.5) and anti-α4β7 (PE). Numbers in the upper right quadrant represent the frequency of $CD8^+$ T cells which express the α4β7 marker. The isotype control percentage was subtracted in all cases. n/group=5. Data are representative of two independent experiments.

FIG. 8 shows that Omp16S, when administered as oral adjuvant, induces a T cellular immune response in vivo. DTH reaction was determined in response to inoculation of 20 μg OVA into the right footpad of animals orally immunized as in FIG. 7. Bars represent the mean fold increment of the footpad skin between right and left foot±SEM at 48 h (A) and 72 h (B), n/group=5, representing 2 experiments with similar results.

FIG. 9 shows that Omp19S, when administered as nasal adjuvant, induces a cellular immune response with cytokine (IFN-γ) production in response to the antigen. C57BL/6 mice were immunized by the nasal route with: (i) OVA, (ii) Omp19S+OVA, or (iii) TC+OVA. Splenocytes of each group (n/group=5) immunized as described in FIG. 7 were stimulated in vitro with 500 μg/ml of OVA or complete medium (RPMI). The culture supernatants were harvested 5 days after stimulation. Cytokine concentrations (A) IFN-γ, (B) IL-4 and (C) IL-10 (pg/ml) in the culture supernatants were determined by ELISA. n/group=5. Values represent the mean of determinations made by duplicate for each mouse±SEM, representing 2 experiments with similar results.

Figure 9:
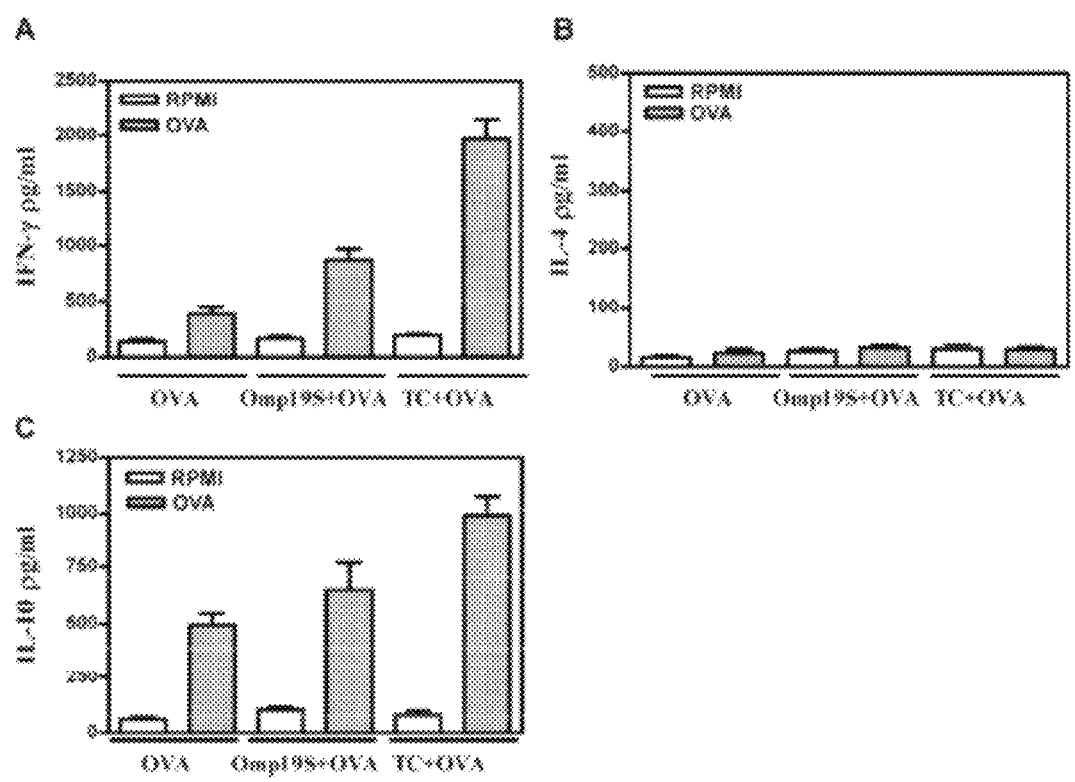
Figure 10:
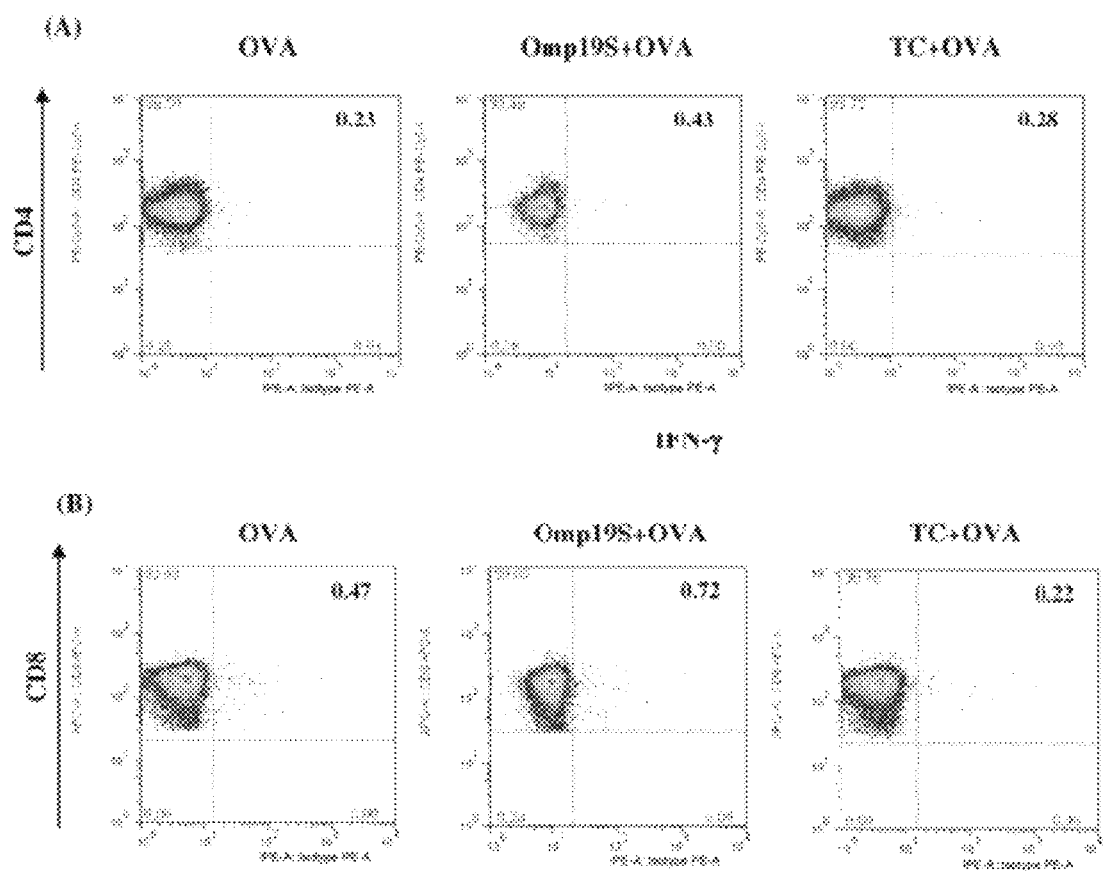

FIG. 10 shows that Omp19S, when administered as nasal adjuvant, stimulates the induction of CD4+ and CD8+ specific T cells which produce IFN-γ. Splenocytes of animals immunized as described in FIG. 9 were cultured with OVA$_{257}$+MO5+OVA 500 μg/ml or with complete medium (no stimulation, RPMI) for 18 h. Then, they were treated with Brefeldin A for the last 4 h of culture. Then, cells were stained with specific anti-CD4 (PE/Cy5) and anti-CD8 (Alexa Fluor 647) Abs. Subsequently, they were fixed, permeabilized and incubated with an anti-IFN-γ (PE) Ab. Numbers in the upper right quadrant represent the frequency of CD4+ (A) or CD8+ (B) T cells expressing IFN-γ. The isotype control frequency and the production of IFN-γ by unstimulated cells of the same group were subtracted in all cases. This way, the indicated percentage corresponds to the production of OVA specific IFN-γ. Data are representative of two independent experiments.

Figure 11:
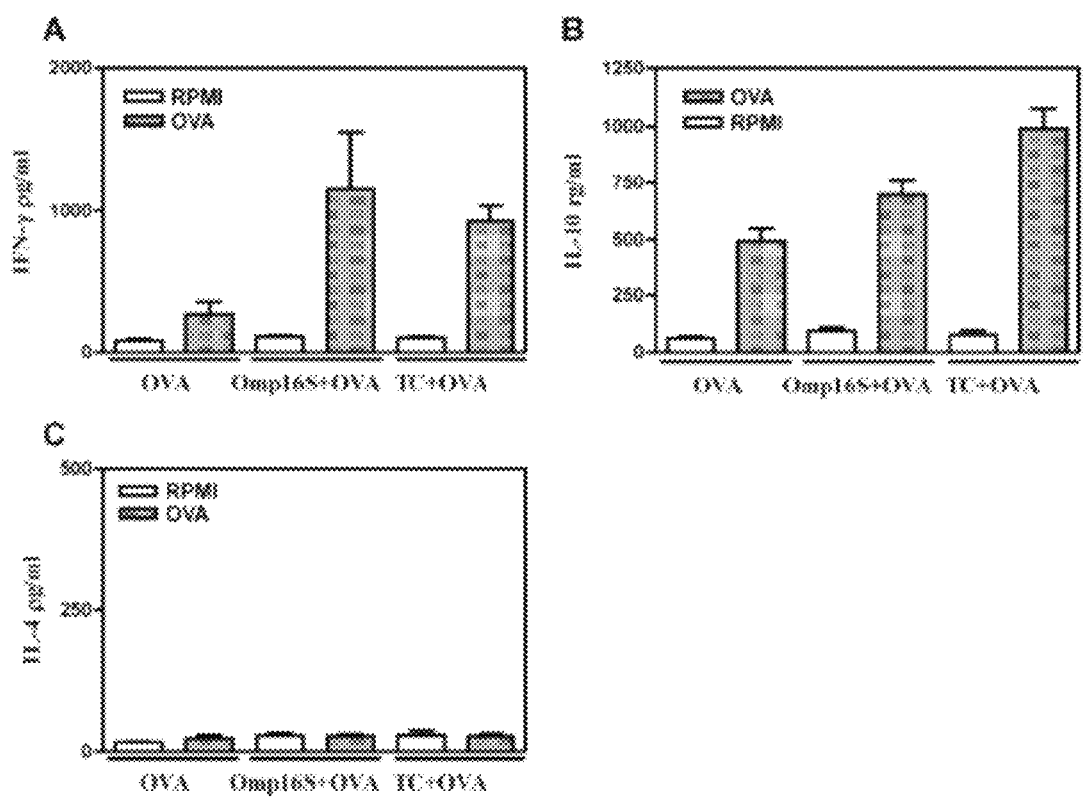

FIG. 11 shows that Omp16S induces a cellular immune response with cytokine production when administered as nasal adjuvant. Animals were immunized by the nasal route with: (i) OVA, (ii) Omp16S+OVA, or (iii) TC+OVA. Splenocytes of each immunized group (n/group=5) were stimulated in vitro with 500 μg/ml of OVA or complete medium (RPMI). The culture supernatants were harvested 5 days after stimulation. Cytokine concentrations (A) IFN-γ, (B) IL-4 and (C) IL-10 (pg/ml) in the culture supernatants were determined by ELISA. n/group=5. Values represent the mean of determinations made by duplicate for each mouse±SEM, representing 2 experiments with similar results.

Figure 12:
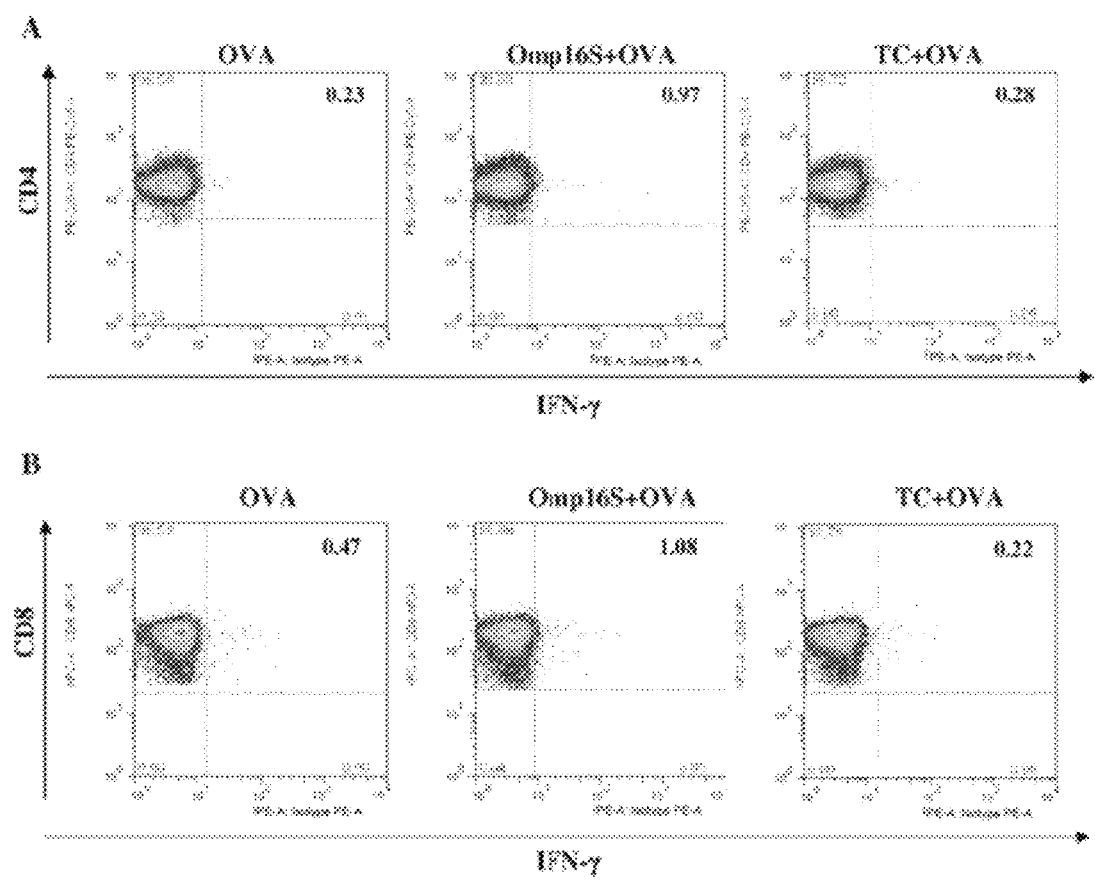

FIG. 12 shows that Omp16S, when administered as nasal adjuvant, stimulates the induction of CD4+ and CD8+ specific T cells which produce IFN-γ. Splenocytes of animals immunized as described in FIG. 11 were cultured either with OVA$_{257}$+MO5+OVA 500 μg/ml or complete medium for 18 h. Then, they were treated with Brefeldin A for the last 4 h of culture. Then, cells were stained with specific anti-CD4 (PE/Cy5) and anti-CD8 (Alexa Fluor 647) Abs. Subsequently, they were fixed, permeabilized and incubated with an anti-IFN-γ (PE) Ab. Numbers in the upper right quadrant represent the frequency of CD4+ (A) or CD8+ (B) T cells expressing IFN-γ. The isotype control frequency and the production of IFN-γ by unstimulated cells of the same group were subtracted in all cases. This way, the indicated percentage corresponds to the production of OVA specific IFN-γ. Data are representative of two independent experiments.

Figure 13:
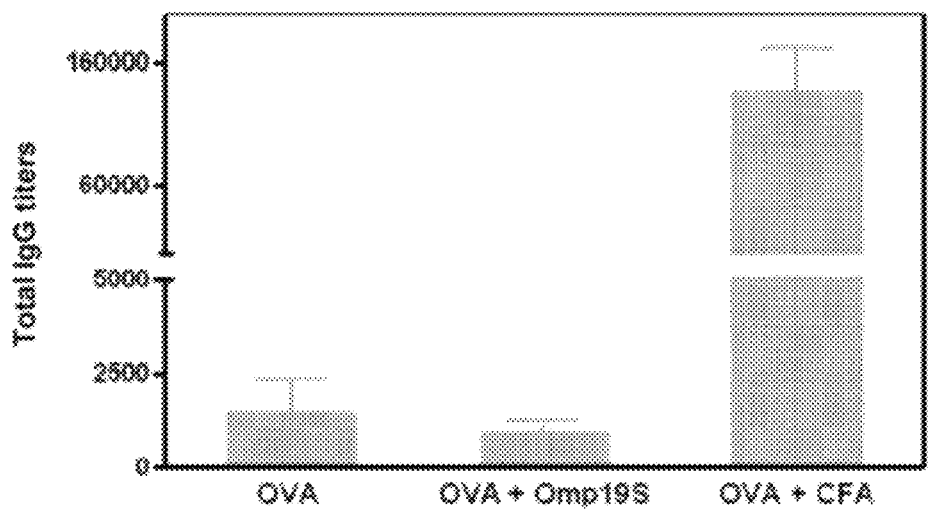

FIG. 13 shows that administration of Omp19S as parenteral adjuvant has no effect on the magnitude of the humoral response. The anti-OVA total IgG titers were determined in sera from BALB/c mice immunized by the subcutaneous route with (i) OVA, (ii) OVA+Omp19S and (iii) OVA+CFA and were determined by ELISA. n/group=5, values represent the mean of determinations made for each mouse±SEM, representing 2 experiments with similar results.

Figure 14:
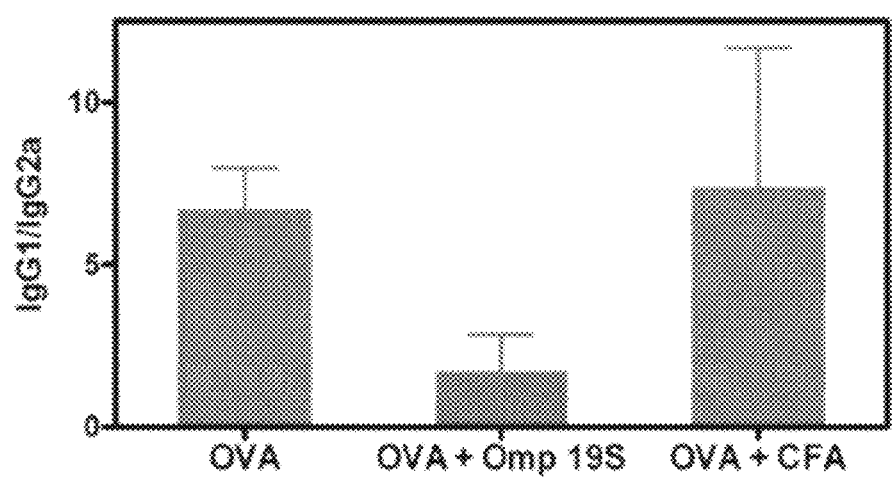

FIG. 14 shows that administration of Omp19S as parenteral adjuvant has an effect on the isotype profile of induced Abs. The isotype ratio IgG1/IgG2a anti-OVA was determined in the sera of animals immunized as described in FIG. 13. Values represent the mean of determinations made for each mouse±SEM. n/group=5, representing 2 experiments with similar results.

Figure 15:
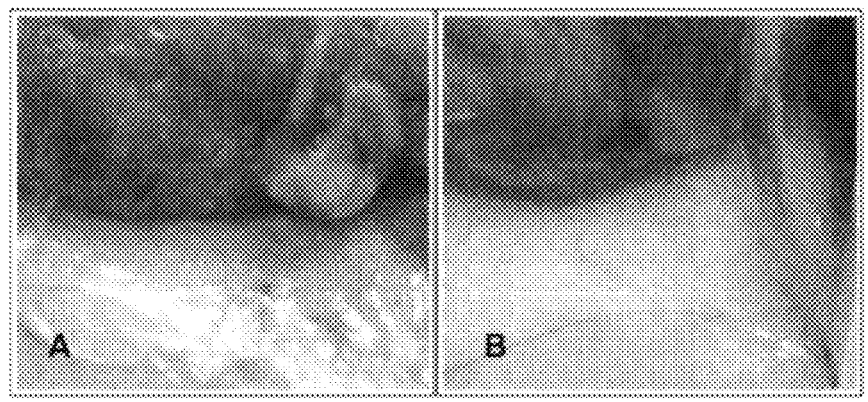

FIG. 15 shows that Omp19S as parenteral adjuvant does not induce local toxicity in the subcutaneous tissue of BALB/c mice after immunizations as described in FIG. 13. A granuloma at the injection site (box) is observed in the mouse immunized with CFA as adjuvant (A). At the right, the same zone in a mouse immunized with Omp19S as a subcutaneous adjuvant is observed, with no alteration signs in the tissue (B).

Figure 16:
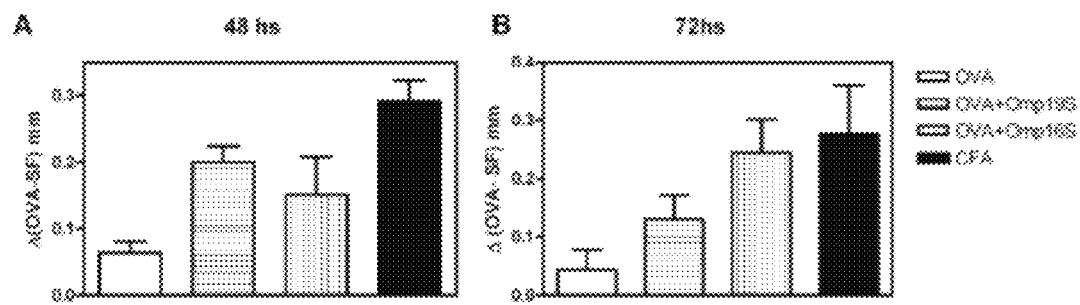

FIG. 16 shows that Omp16S and Omp19S, when administered as parenteral adjuvants, induce a T cellular immune response against the antigen in vivo. DTH reaction was determined in response to a challenge with 20 μg OVA into the right footpad of animals subcutaneously immunized with (i) OVA, (ii) OVA+Omp16S, (iii) OVA+Omp19S or (iv) OVA+CFA as described in FIG. 13. Bars represent the mean fold increase of the footpad skin between right and left foot±SEM at 48 hs (A) and 72 hs (B) after challenge with OVA. n/group=5, representing 3 experiments with similar results.

Figure 17:
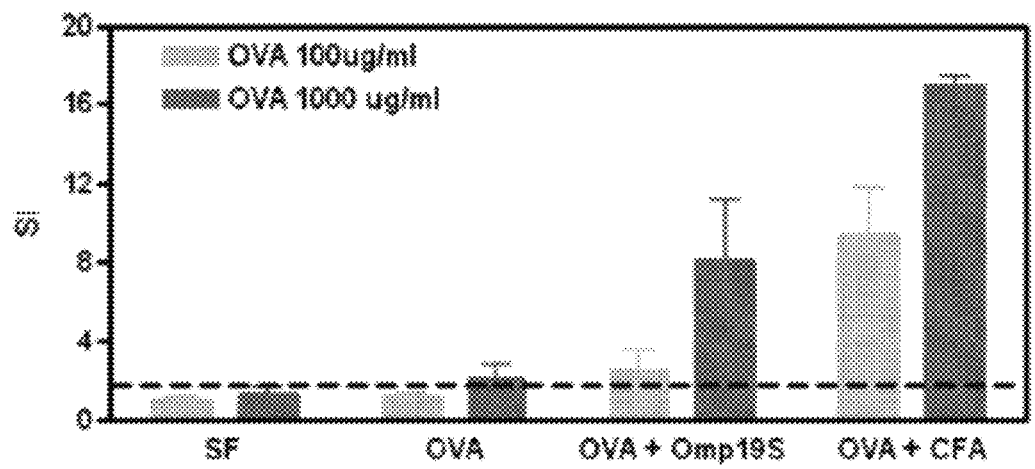

FIG. 17 shows that Omp19S, when administered as parenteral adjuvant, induces an increase in the proliferation of splenocytes in response to the Ag. In vitro proliferation was assessed as a response to different doses of OVA in the splenocytes of mice immunized as described in FIG. 13. Results were expressed as stimulation index SI (OVA cpm/RPMI cpm). n/group=5. Values represent the mean of determinations made by triplicate for each mouse±SEM, representing 2 experiments with similar results.

Figure 18:
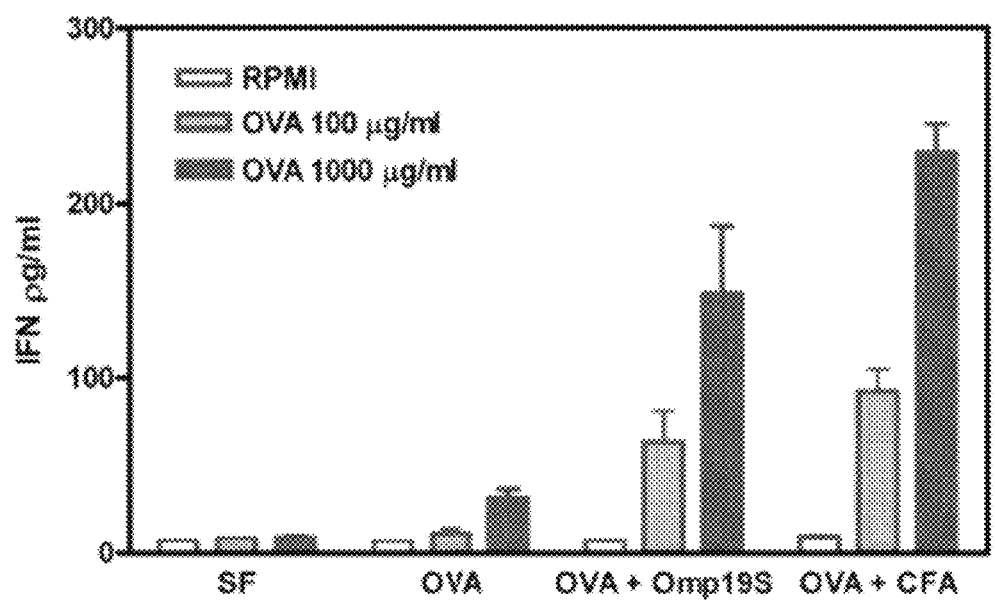

FIG. 18 shows that Omp19S, when administered as parenteral adjuvant, induces a cellular immune response with cytokine (IFN-γ) production after antigenic stimulation. IFN-γ production by splenocytes of mice immunized as described in FIG. 13, stimulated in vitro for 72 h with different OVA concentrations or complete medium, was determined. n/group=5. Values represent the mean of determinations made by duplicate for each mouse±SEM, representing 2 experiments with similar results.

Figure 19:
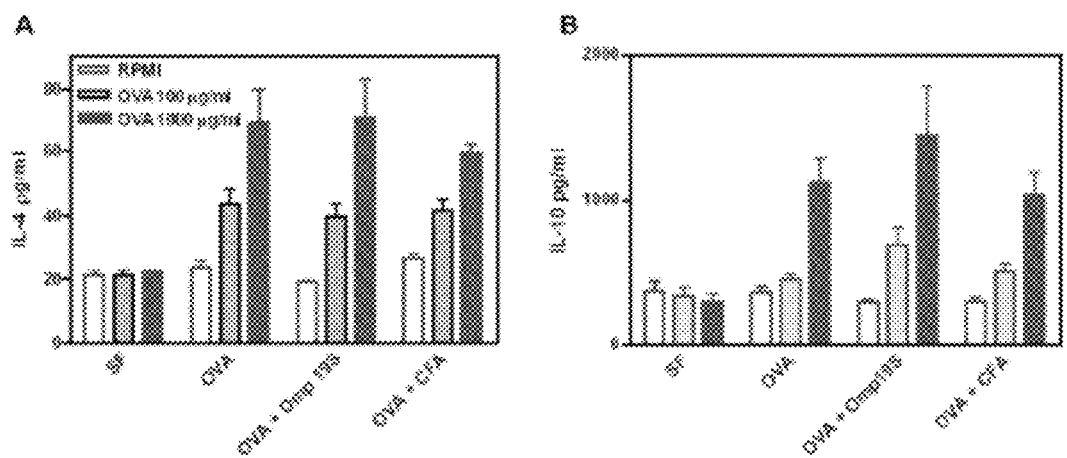

FIG. 19 shows that Omp19S, when administered as parenteral adjuvant, does not induce an increase in IL-4 nor in IL-10 production, in response to the antigen. IL-4 (A) and IL-10 (B) production by the splenocytes of mice immunized as described in FIG. 13, stimulated in vitro for 72 h with different OVA concentrations or complete medium (RPMI), was evaluated. n/group=5. Values represent the mean of determinations made by duplicate for each mouse±SEM, representing 2 experiments with similar results.

Figure 20:
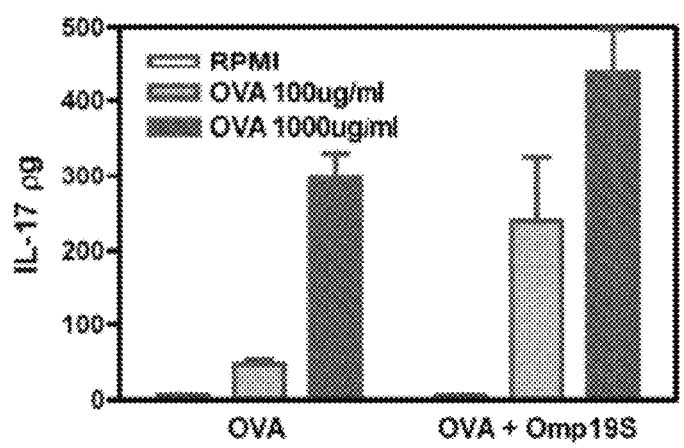

FIG. 20 shows that Omp19S, when administered as parenteral adjuvant, induces a cellular immune response with IL-17 production in response to the antigen. IL-17 production by splenocytes of mice immunized as described in FIG. 13, stimulated in vitro for 72 h with different OVA concentrations or complete medium (RPMI), was determined. n/group=5. Values represent the mean of determinations made by duplicate for each mouse±SEM, representing 1 experiment.

Figure 21:
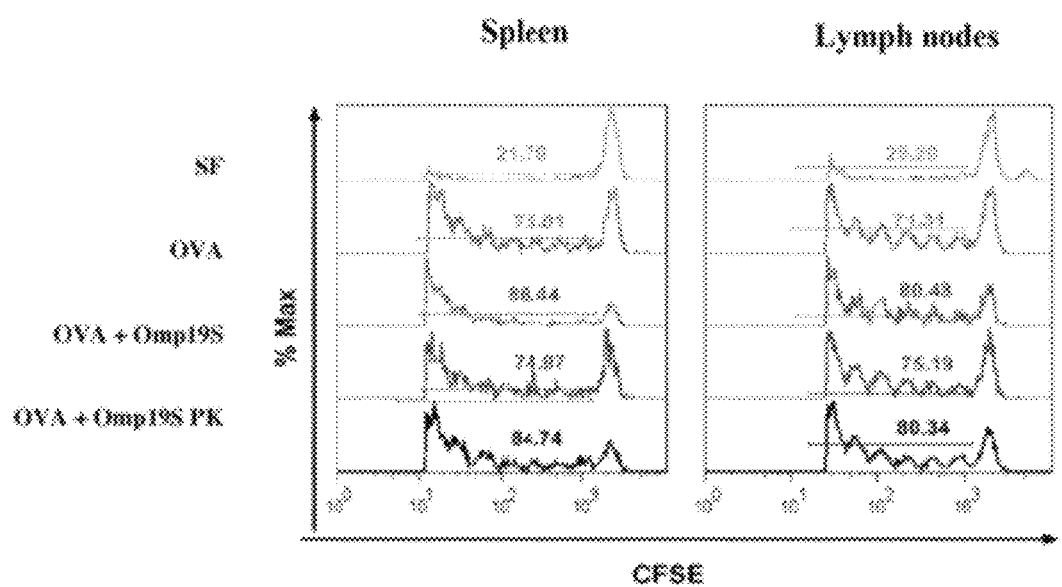

FIG. 21 shows that the use of Omp19S as an adjuvant by parenteral route increases the proliferation of CD8+ cells specific for OVA$_{257-264}$. Cells from OT-1 mice were marked with carboxyfluorescein succinimidyl ester (CFSE) and transferred intravenously (i.v.) (10×10$^6$ cells/mouse) to C57BL/6 mice. One day after adoptive transfer, the receptor C57BL/6 mice were subcutaneously (s.c.) immunized with: (i) OVA, (ii) OVA+Omp19S, (iii) OVA+Omp19S degraded with proteinase K (Omp19SPK) or (iv) OVA+LPS. The proliferation of cells from OT-1 CFSE+ in spleen and lymph nodes was determined 5 days after immunization by flow cytometry analyzing the dilution of CFSE fluorescence. The percentage of CD8+ cells that underwent more than one division is shown, representing results of 3 experiments.

Figure 22:
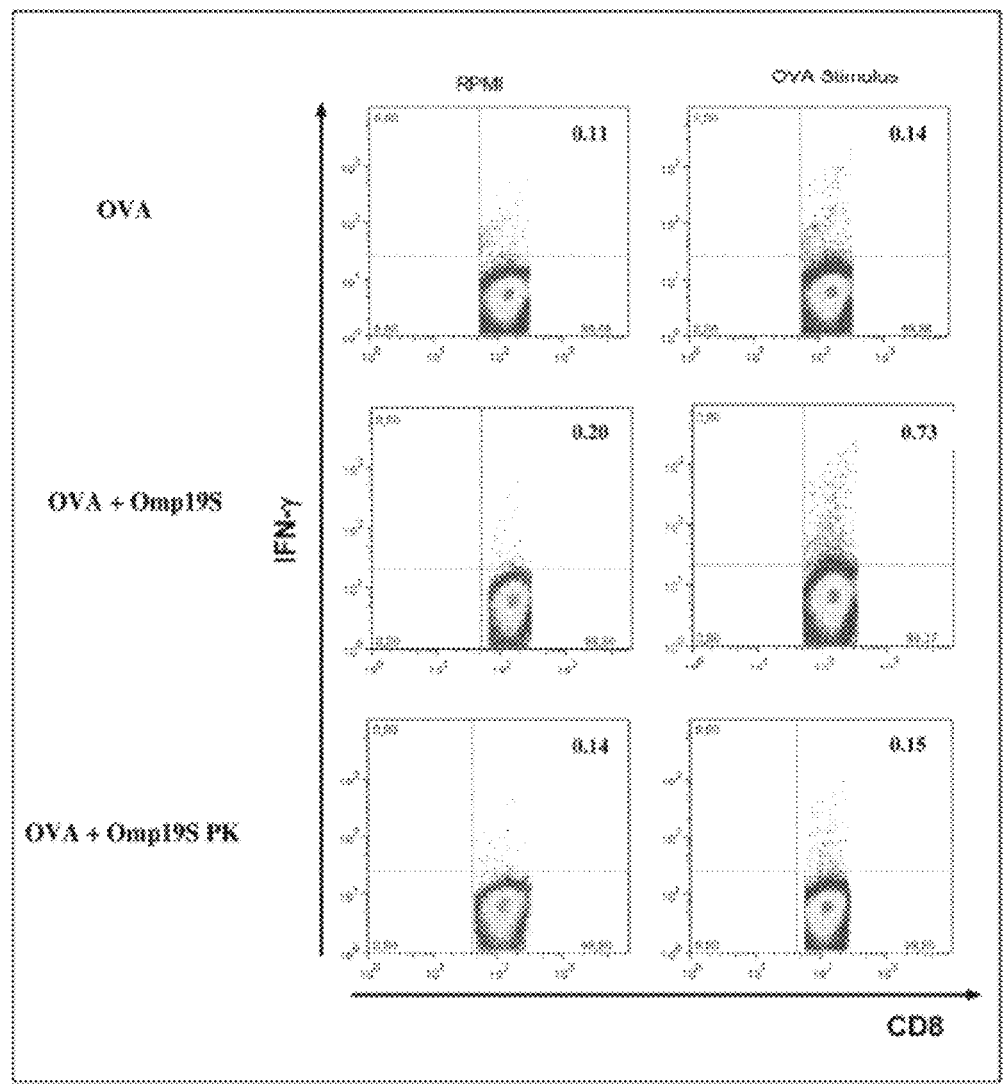

FIG. 22 shows that the use of Omp19S as an adjuvant by parenteral route increases the intracellular production of IFN-γ in the CD8+ cell population specific for $OVA_{257-264}$. Splenocytes from immunized animals as described in FIG. 22 were stimulated for 18 h with: complete medium (RPMI), OVA 500 µg/ml+SIINFEKL peptide (SEQ ID NO: 11) 5 µg/ml+MO5, and then treated with Brefeldin A for 6 h. Then, cells were stained with anti-CD8 Alexa Fluor and anti-IFN-γ PE antibodies. Values in the upper right quadrant represent the frequency of IFN-γ-producing CD8+ (B) cells.

Figure 23:
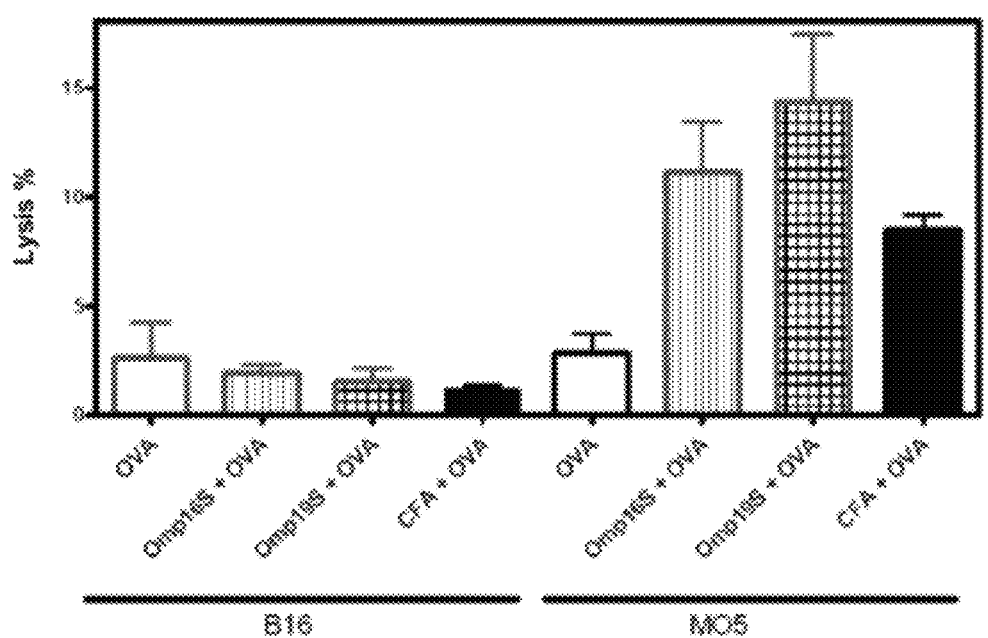

FIG. 23 shows that immunization with Omp16S or Omp19S as adjuvants induces a cytotoxic immune response capable of lysing tumor cells expressing the Ag. The cytotoxic activity of the splenocytes from C57BL/6 mice immunized with: (i) OVA, (ii) Omp16S+OVA, (iii) Omp19S+OVA, or (iv) CFA+OVA, was determined. Target cells (MO5 expressing OVA or B16 not expressing OVA) marked with $^{51}Cr$ were incubated with splenocytes in a ratio 50 splenocytes:1 target cell. After 6 h, cpm in the supernatants was measured and the results were analyzed according to the specific lysis percentage.

Figure 24:
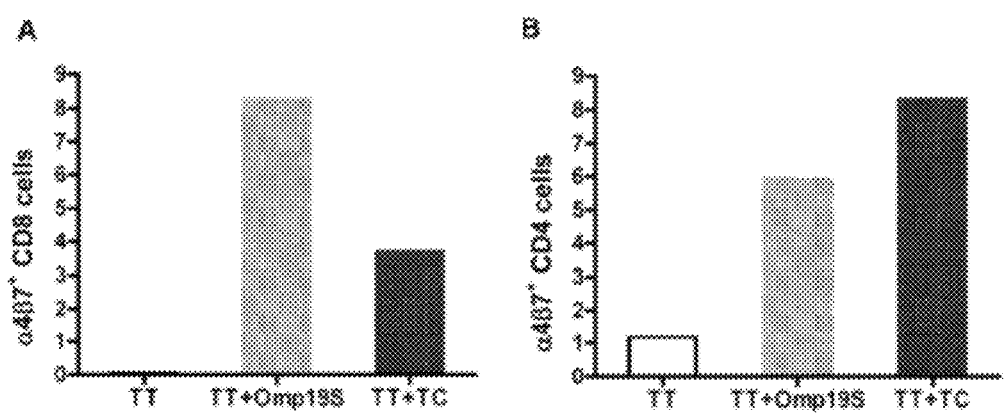

FIG. 24 shows that the frequency of CD4+ and CD8+ T cells expressing α4β7 increases in mesenteric lymph nodes of BALB/c mice immunized by the oral route with Omp19S as adjuvant. The animals were orally immunized with: (i) tetanus toxoid (TT), (ii) TT+Omp19S or (iii) TT+TC. $2 \times 10^6$ mesenteric lymph node cells derived from each immunization group were stained with anti-CD4 (FITC), anti-CD8 (PE-Cy5.5) and anti-α4β7 (PE) antibodies. Numbers in the upper right quadrant represent the frequency of CD8+ (A) and CD4+ (B) T cells which express the α4β7 marker. The isotype control frequency was subtracted in all cases. n/group=5.

Figure 25:
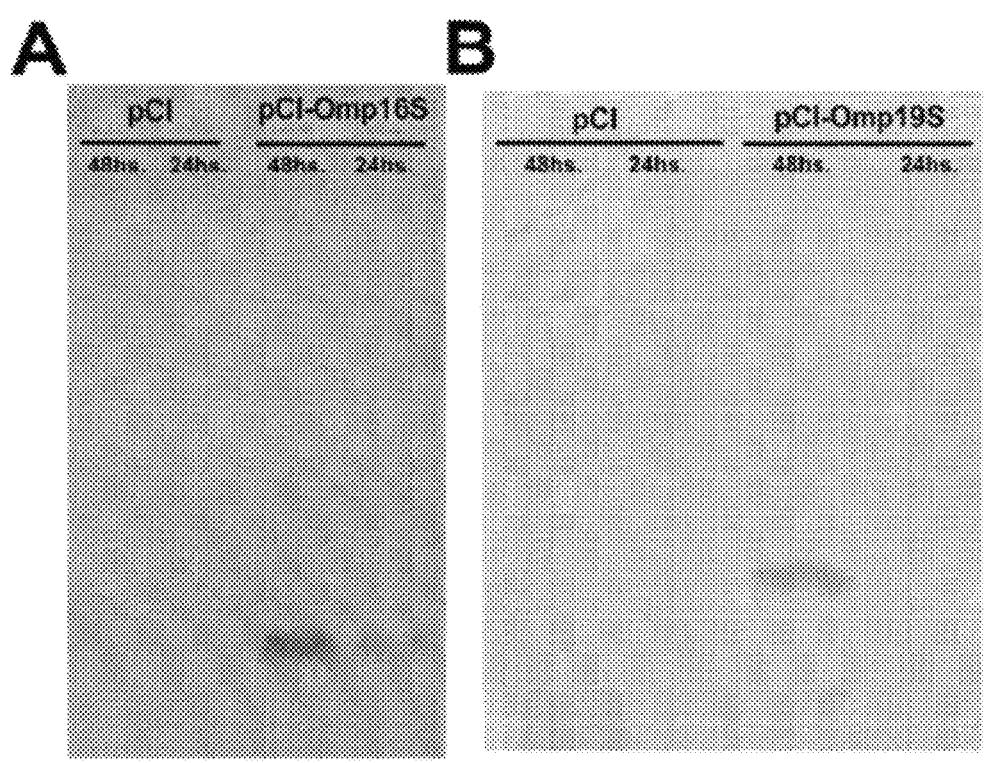

FIG. 25 shows in gels that the Omp16S and Omp19S proteins are correctly expressed in eukaryote cells transfected with the eukaryotic expression plasmids pCI-Omp16S or pCI-Omp19S, respectively. The expression of (A) Omp16S or (B) Omp19S was studied in eukaryotic cells (COS-7) transiently transfected with the plasmids pCI-Omp16S or pCI-Omp19S, respectively or with the plasmid pCI as a control. After 24 or 48 h of culture, the expression of Omp16 or Omp19 was assessed by Western Blot in protein extracts from transfected cells using specific anti-Omp16 or anti-Omp19 antibodies, respectively.

Figure 26:
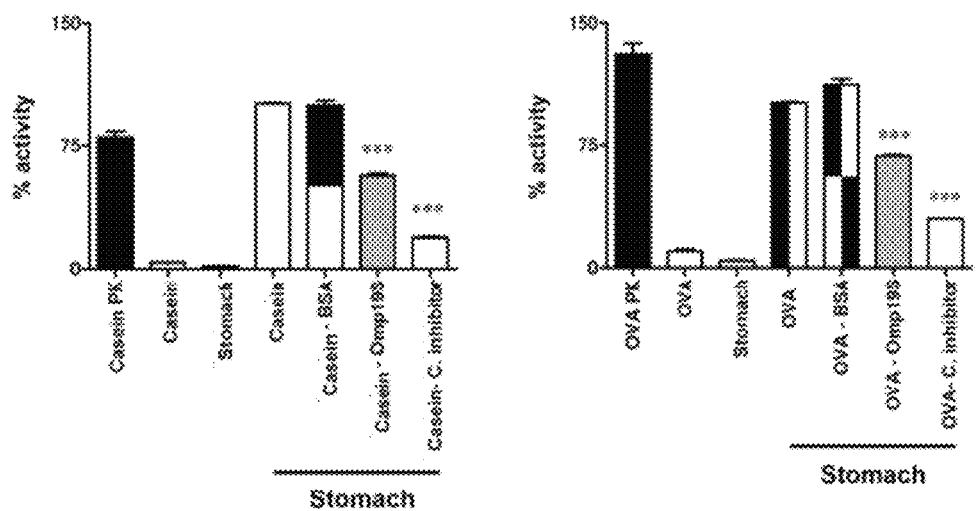

FIG. 26 shows that Omp19S inhibits the stomach proteases of BALB/c mice. The supernatants of the stomach extracts were incubated with BSA (irrelevant protein), Omp19S, mammal protease inhibitor cocktail (as a control that stomach enzymatic activity may be inhibited). Enzymatic activity was measured using BODIPY FL casein or BODIPY FL OVA as substrates. The graphic represents the percentage of residual enzymatic activity after each treatment, calculated by considering as the maximum activity that of the stomach extract supernatant over the BODIPY FL casein or BODIPY FL OVA substrate, as appropriate. The fluorescent capacity of the BODIPY FL casein or BODIPY FL OVA substrates, once degraded, was checked by treating these substrates with PK (proteinase K).

Figure 27:
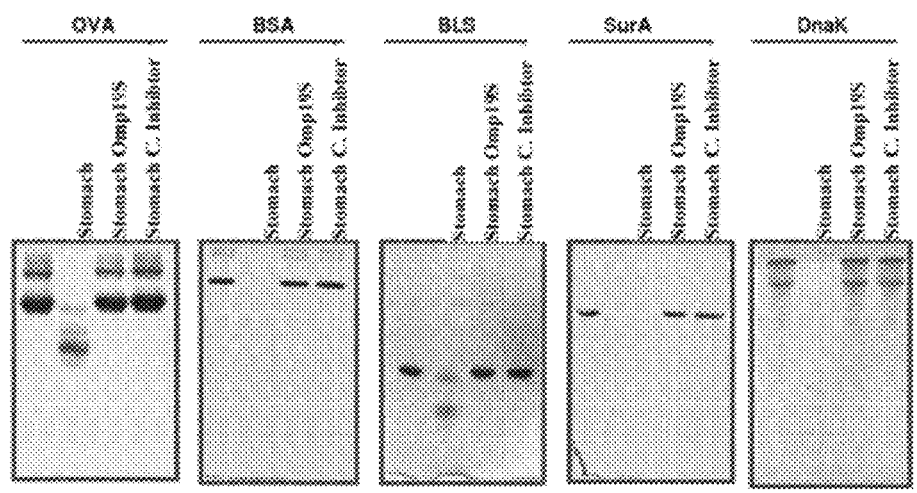

FIG. 27 shows that Omp19S is capable of inhibiting the degradation of eukaryotic (BSA, OVA) and bacterial (BLS, SurA. DnaK) antigens by the stomach proteases of BALB/c mice. Each antigen was treated with: (i) stomach extract supernatant, (ii) stomach extract supernatant and Omp19S, (iii) stomach extract supernatant and mammal protease inhibitor cocktail (as a control that stomach enzymatic activity may be inhibited). These reaction mixtures were subjected to a sodium dodecyl sulfate polyacrylamide gel electrophoresis (SDS-PAGE) and subsequent Coomasie blue staining.

Figure 28:
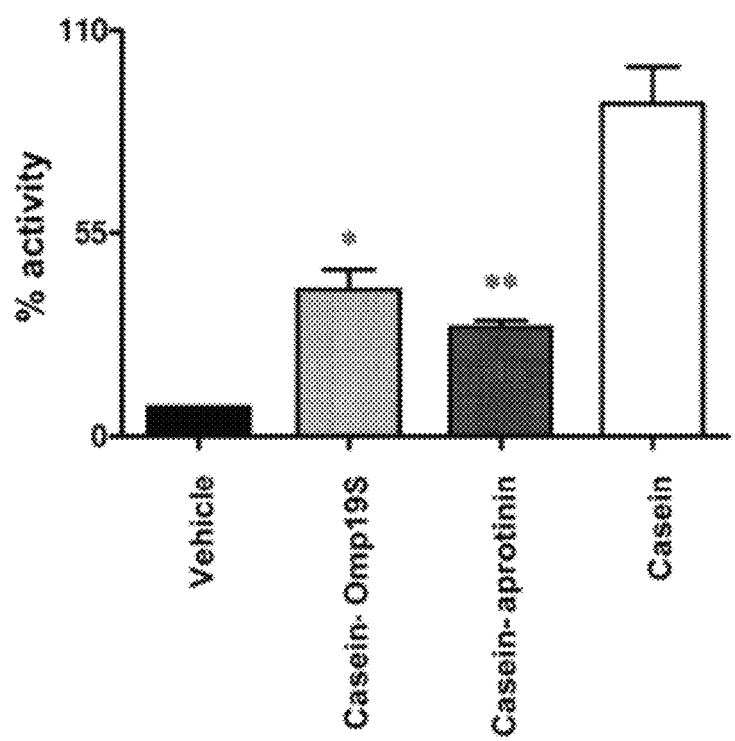

FIG. 28 shows the capacity of Omp19S for inhibiting the degradation of antigens by the stomach proteases in vivo, using as an antigen model the BODIPY FL casein. BALB/c mice were inoculated orally with: (i) $NaHCO_3$ buffer (1M, pH8) (vehicle), (ii) BODIPY FL casein with Omp19S, (iii) BODIPY FL casein with aprotinin (a known protease inhibitor), iv) BODIPY FL casein. The graphic represents the percentage of residual enzymatic activity after each treatment, calculated by taking as the maximum activity that of the stomach extract supernatant of mice immunized with BODIPY FL casein.

DETAILED DESCRIPTION OF THE INVENTION

For the purposes of the present application, the phrases "Omp19S polypeptide", "Omp19S protein" and "Omp19S" have the same meaning and correspond to the non-lipidated Omp19S polypeptide.

The term Omp19S or Omp16S refers to the polypeptide sequence which may correspond to the SEQ No. 1 or SEQ No. 2, respectively, which is obtained by purification from cells, tissues or organisms expressing it, or by chemical synthesis.

For the purposes of the present application, the phrases "Omp16S polypeptide", "Omp16S protein" and "Omp16S" have the same meaning and correspond to the non-lipidated Omp16S polypeptide.

In the present application, the term "immunogen" and "antigen" have the same meaning and are defined as any substance against which, in an immunocompetent organism, a humoral or cellular immune response may be induced. According to this meaning, antigen is a synonym of immunogen.

Figure 1:
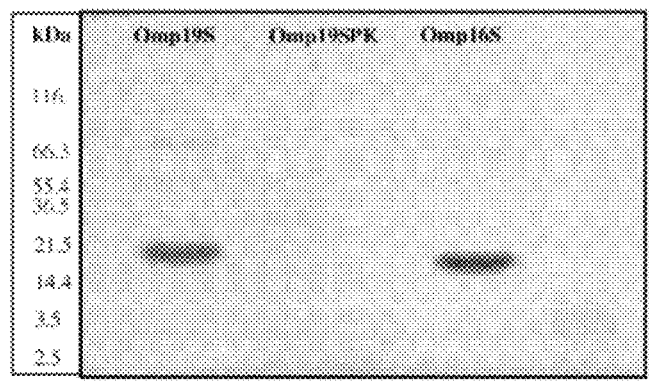
Figure 2:
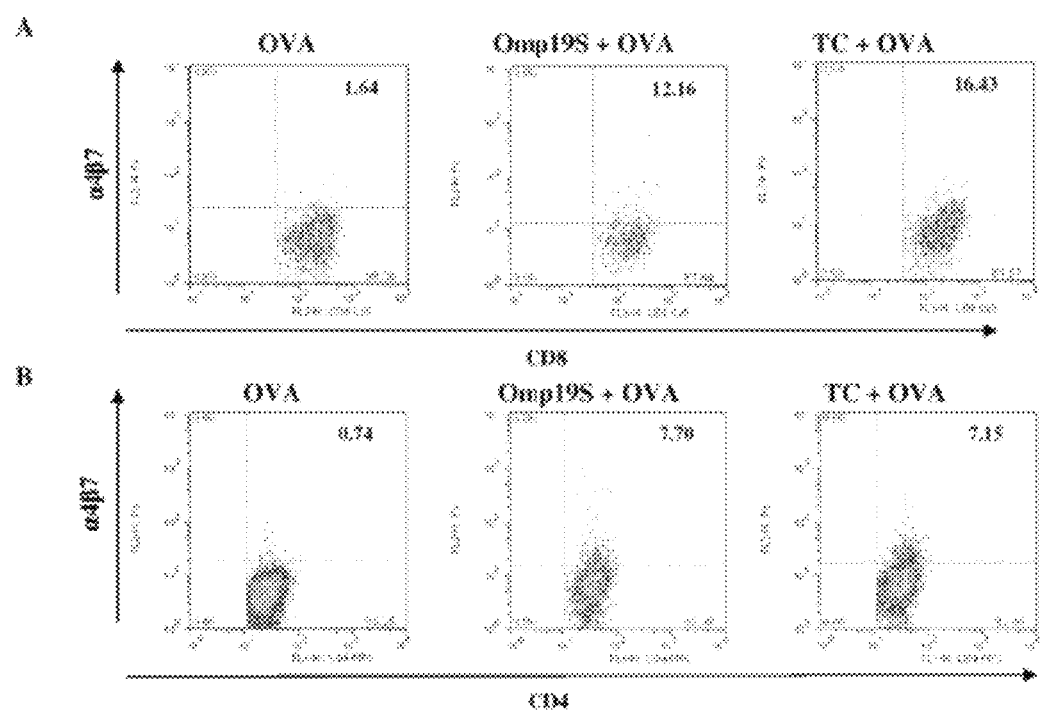
Figure 3:
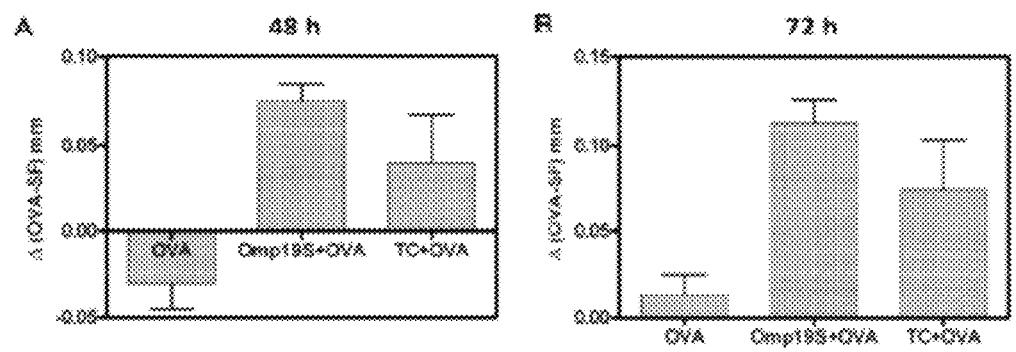
Figure 4:
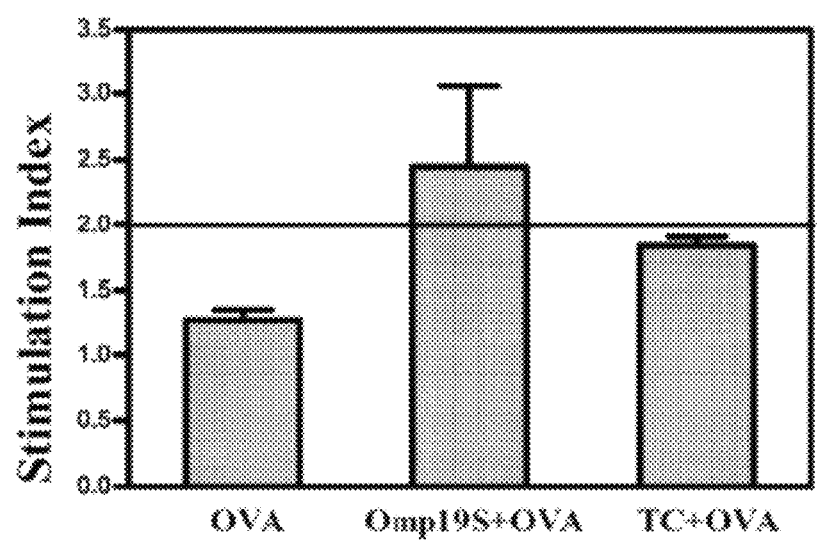
Figure 5:
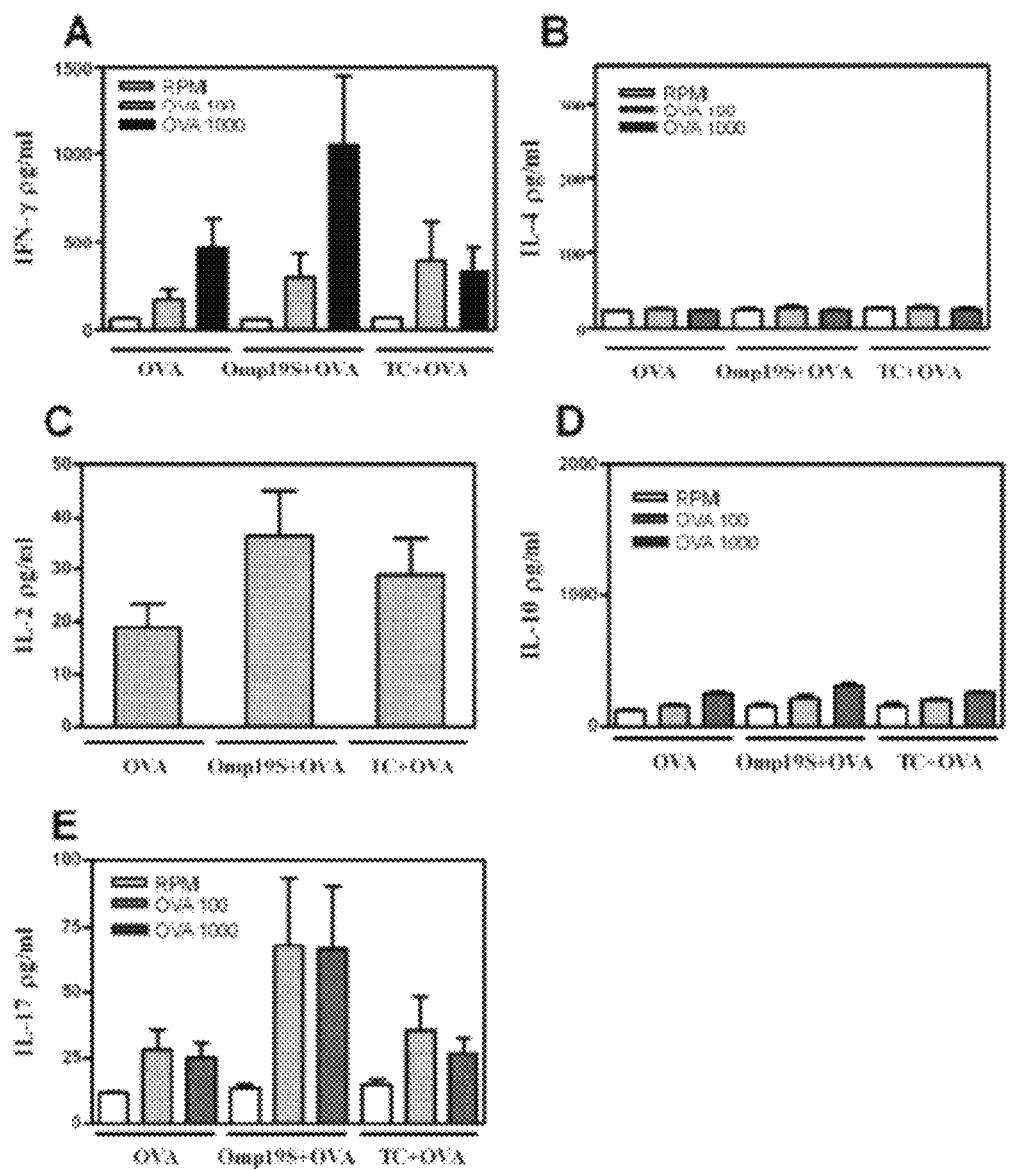

In a preferred embodiment, the Omp19S polypeptide was cloned without the lipidation consensus sequence into a plasmidic vector. Using this construct, competent E. coli cells were transformed so as to express and purify the non-lipidated polypeptide. Purification was performed using a nickel-agarose resin. The corresponding eluates were seeded in a SDS polyacrylamide gel (FIG. 1). Subsequently, the eluates with similar concentration were pooled in different fractions. In these fractions, the identity of the purified polypeptide was confirmed by performing a Western Blot using a monoclonal antibody against Omp19.

The cloned polypeptide was sequenced and its sequence is shown in SEQ ID No: 1. It shall be apparent that variations to said sequence may exist, all of them falling within the scope of the present invention. For example, fragments thereof, or additions or deletions of fragments or amino acids. Also encompassed within the scope of the present invention are the Omp19S non-lipidated polypeptides obtained from any Brucella species.

In another preferred embodiment, the Omp16S polypeptide was cloned without the lipidation consensus sequence in a plasmidic vector. Using this construct, competent E. coli cells were transformed so as to express and purify the non-lipidated polypeptide. Purification was performed using a nickel-agarose resin. The corresponding eluates were seeded in a SDS polyacrylamide gel (FIG. 1). Subsequently, the eluates with similar concentration were pooled in different fractions. In these fractions, the identity of the purified polypeptide was confirmed by performing a Western Blot using a monoclonal antibody against Omp16S. The cloned polypeptide was sequenced and its sequence is shown in SEQ ID No: 2. It shall be apparent that variations to said sequence may exist, all of them falling within the scope of the present invention. For example, fragments thereof, or additions or deletions of fragments or amino acids. Also encompassed within the scope of the present invention are the Omp16S non-lipidated polypeptides obtained from any *Brucella* species.

Figure 6:
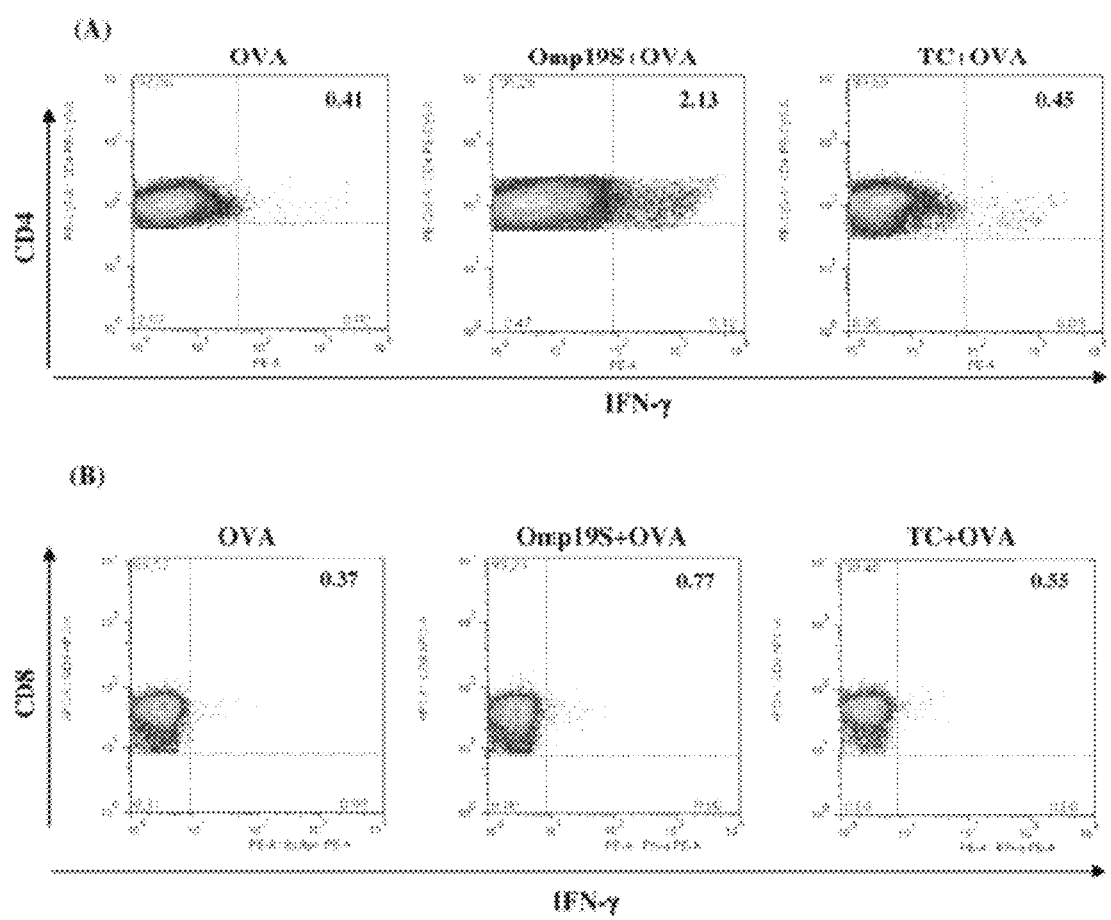

From the disclosure of the present applications it shall be obvious that other *Brucella* Omp polypeptides could be used as adjuvants, provided that they are in a non-lipidated form. The non-lipidated form may be obtained through modifications in the peptidic skeleton, as well as by other known methods. Any non-lipidated Omp polypeptide is encompassed within the scope of the present invention.

Assays Using Mucosal Omp19S or Omp16S:

The $\alpha4\beta7$ expression in $CD4^+$ and $CD8^+$ T lymphocytes of mesenteric lymph nodes from animals orally immunized with: (i) OVA (ovalbumin), (ii) Omp19S+OVA, or (iii) cholera toxin (TC)+OVA, was assessed.

Results indicate that there was an increase in the frequency of $CD4^+$ and $CD8^+$ T lymphocytes expressing the mucosal migration marker (gastrointestinal lamina propria) $\alpha4\beta7$ in the mesenteric lymph nodes of those animals inoculated orally with Omp19S+OVA (7.7%; 12.16%) and TC+OVA (7.15%; 16.43%) as adjuvants, when compared to the administration of the antigen without the adjuvant OVA (0.74%; 1.64%) (FIGS. 2 A and B). Therefore, it can be said that Omp19S administered orally would induce migration of $CD4^+$ and $CD8^+$ effector T lymphocytes to the intestinal mucosa.

The delayed-type hypersensitivity response (DTH) is mediated by T cells that migrate to the antigen injection site, recognize peptides derived from that antigen on the antigen-presenting cells (APCs) and release cytokines such as IFN-γ, which stimulates the recruitment of cells of the innate immune system causing edema and swelling. Then, in order to analyze the T response in vivo, the DTH response induced by OVA injection was evaluated in mice immunized orally with the adjuvants of the invention. To this end, 20 μg OVA were injected into the footpad of one of the legs of immunized mice and a physiological solution was injected in the other leg as a control. Those animals immunized orally with OVA co-administered with Omp19S presented an increase in the footpad skin with respect to those animals immunized with OVA without adjuvant at 48 h and 72 h post-OVA injection (FIGS. 3 A and B). This increase was slightly higher to the one induced by the cholera toxin as adjuvant administered by the same route (FIGS. 3 A and B).

These results show that the Omp19S adjuvant administered orally would be capable of inducing a cellular response in vivo which is similar to or higher than the one generated by an experimental known mucosal adjuvant such as the cholera toxin. Omp19S as adjuvant of the mucosa would induce an anti-antigen (OVA) T cell response in vivo.

In order to characterize the cellular immune response induced, the capacity of splenocytes of immunized animals to proliferate in vitro was determined in response to antigenic stimulation. Cells were cultured in the presence of different OVA concentrations or complete medium. After 5 days a $^3$H-tymidine pulse was given for 18 h and the incorporated radioactivity was measured. The results obtained show that oral co-administration of OVA and Omp19S adjuvant induced an increase in the antigen-specific proliferative response of cells from these mice compared to those of animals immunized only with OVA (FIG. 4). Stimulation with Concanavalin A (ConA, control mitogen) caused significant increase in cell proliferation. On the contrary, the use of cholera toxin as adjuvant did not induce an increase in the proliferative capacity of splenocytes as a response to the Ag. These results would indicate that the use of the Omp19S adjuvant orally would have an effect on the generation of an efficient adaptive response evidenced by an increase in the antigen-specific proliferative response of T cells.

Based on the DTH and proliferation results, a cellular response developed as a response to the stimulation with the antigen, was evidenced.

Subsequently, the T response profile developed in animals when orally immunized with the adjuvant of the invention was characterized.

For the determination of the type of anti-OVA T helper (Th) response induced by Omp19S as adjuvant, splenocytes from immunized mice were cultured in the presence of different concentrations of OVA or complete medium for 72 h and then, the pattern of the cytokines produced was analyzed in the supernatant of these cells. A capture ELISA was performed using specific monoclonal antibodies for the detection of IFN-γ, IL-2, IL-10, IL-4 and IL-17 in the culture supernatants of stimulated and control splenocytes.

Results indicate that the cells of animals orally immunized with OVA+Omp19S produced higher amounts of IFN-γ, IL-2 and IL-17 than cells of control animals (OVA) and than cells of animals immunized with OVA+TC (FIG. 5). Moreover, secretion of these cytokines was antigen-specific and dose-dependent.

On the contrary, the levels of Th2 profile cytokines as IL-4 and IL-10 were similar to basal levels. This way, the use of Omp19S as adjuvant by the oral route would generate a Th1- and Th17-type response.

It is not only important the amount of the induced response induced by an adjuvant but also the quality of this response. Given that the lymphocytes of mice co-immunized with Omp19S+OVA released IFN-γ, the $CD4^+$ or $CD8^+$ T cell subpopulation producing this cytokine was assessed. To this end, the intracellular production of IFN-γ by the $CD4^+$ and $CD8^+$ T cells was determined.

For this purpose, a 16 h incubation protocol with different stimuli was performed. In order to stimulate the lymphocytes extracted from mouse spleen, MHC class II-restricted OVA peptide for BALB/c ($OVA_{323}$), antigen presenting cells A20J and OVA (500 μg/ml) were used. Other stimuli consisted in complete medium (RPMI) as a negative control and Pma/ionomycin (a T cell polyclonal activator) as a positive control. In FIG. 6 the production of IFN-γ in $CD4^+$ T cells by the groups of mice orally immunized with OVA, OVA+Omp19S and OVA+TC, is shown.

The immunization with Omp19S as adjuvant by the oral route induced the production of antigen-specific IFN-γ-producing $CD4^+$ T cells (2.13%) while in the group immunized with TC as adjuvant there was no different production to the group immunized with OVA without adjuvant (OVA+TC 0.45% vs. OVA 0.41%) (FIG. 6 A). As for the IFN-γ-producing $CD8^+$ T lymphocytes, a slight increase may be observed in the group OVA+Omp19S (0.77%) but significant in relation to the group immunized with OVA (0.37%) or with OVA+TC (0.55%) (FIG. 6B).

In summary, the use of Omp19S as oral adjuvant induces (i) the migration of $CD4^+$ and $CD8^+$ T lymphocytes to the gastrointestinal mucosa, (ii) an antigen-specific T cell response in vivo, (iii) the release of cytokines Th1, Th17 as well as the proliferation of lymphocytes as a response to the Ag, and (iv) memory IFN-$\gamma$-producing $CD4^+$ and $CD8^+$ T lymphocytes. These IFN-$\gamma$-producing cells are indispensable for the generation of efficient immune responses against infections by pathogens with an intracellular phase in their life cycle, such as virus, bacteria, parasites and fungi; or tumors. The fact that the adjuvant induces the production of this cytokine by the T lymphocytes could be beneficial for the development of vaccines against these kinds of diseases. All these qualities are largely required in the field of mucosal adjuvants.

Figure 7:
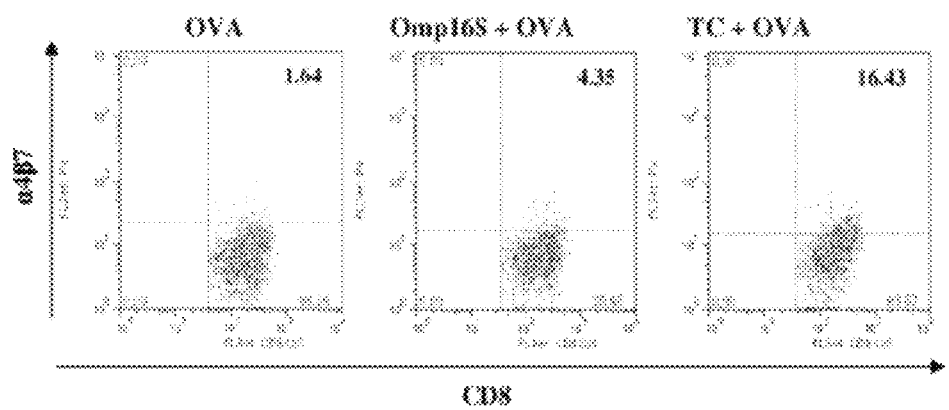

Expression of $\alpha 4\beta 7$ in $CD4^+$ and $CD8^+$ T lymphocytes of mesenteric lymph nodes obtained from animals orally immunized with (i) OVA, (ii) OVA+Omp16S or (iii) OVA+TC was also assessed (FIG. 7). Results indicate that there was increase in the frequency of $CD8^+$ T lymphocytes expressing the mucosal migration marker $\alpha 4\beta 7$ in mesenteric lymph nodes of those animals orally immunized with OVA+Omp16S (4.35%) and OVA+TC (16.43%), when compared to the administration of antigen without adjuvant (OVA, 1.64%). These results suggest that Omp16S administered by the oral route induces the migration of effector $CD8^+$ T lymphocytes to the intestinal mucosa.

Figure 8:
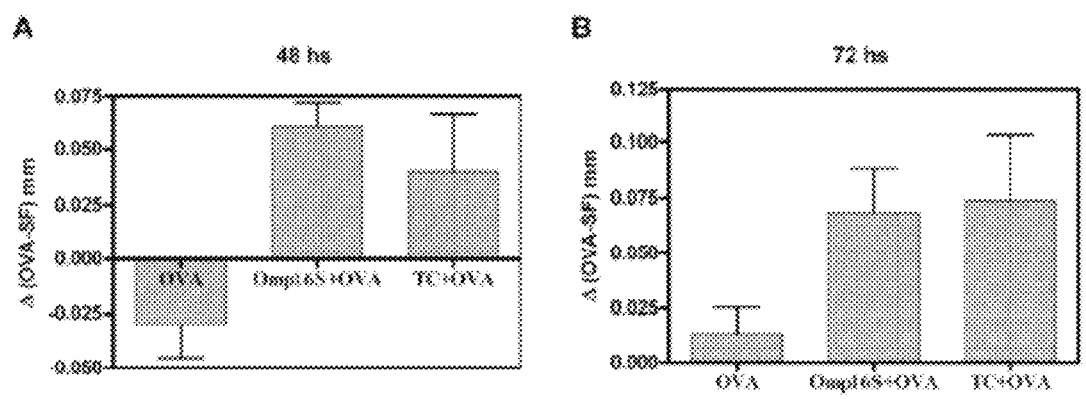

In order to analyze the T cell response in vivo, the delayed-type hypersensitivity response induced by the OVA injection was evaluated in mice immunized by the oral route. Those animals immunized orally with OVA co-administered with Omp16S as adjuvant presented an increase in the footpad skin with respect to those animals immunized with OVA and without adjuvant at 48 h and 72 h post-immunization with OVA (FIGS. 8 A and B). This increase was slightly higher than the one induced by the cholera toxin administered as adjuvant by the same route at 48 h (FIGS. 8 A and B). Thus, Omp16S as mucosal adjuvant induces an anti-antigen (OVA) delayed-type hypersensitivity (DTH) response. Omp16S administered by the oral route is capable of inducing a T cellular response in vivo similar to the one generated with an experimental known mucosal adjuvant such as the cholera toxin.

The use of Omp16S as adjuvant by the oral route would induce (i) the migration of $CD8^+$ T lymphocytes to the gastrointestinal mucosa, (ii) an antigen-specific T cellular response in vivo.

Nasal administration of Omp19S generates the production of OVA specific cytokines in spleen splenocytecultures. Splenocytes from animals immunized nasally with OVA+Omp19S produced higher levels of IFN-$\gamma$ with respect to animals immunized with OVA without any adjuvant (FIG. 9A) as a response to the antigen OVA. Administration of OVA+TC nasally induced higher levels of IFN-$\gamma$ in the culture supernatants of splenocytes stimulated with OVA. On the contrary, stimulation with OVA did not induce secretion of IL-4 in the splenocytes derived from any of the studied groups (FIG. 9B). As for IL-10, a slight increase was detected with respect to the negative control, only in the group immunized with OVA+TC (FIG. 9C). Thus, administration of Omp19S as a nasal adjuvant induces a Th1 cellular immune response with production of IFN-$\gamma$.

Considering the cytokine profile released by splenocytes, it was assessed whether the $CD4^+$ or $CD8^+$ T cells were responsible for this production. To this end, a measurement of intracellular IFN-$\gamma$ 3 weeks after the last immunization was performed.

Immunization with Omp19S as nasal adjuvant (Omp19S+OVA) induced the production of IFN-$\gamma$-producing antigen-specific $CD4^+$ T cells (0.43%) while immunization with TC as adjuvant (TC+OVA) did not induce a different production than that of the group immunized with OVA without any adjuvant (OVA+TC 0.28% vs. OVA 0.23%) (FIG. 10A). As for the IFN-$\gamma$-producing $CD8^+$ T lymphocytes, it may be observed a slight increase in the group OVA+Omp19S (0.72%) but significant compared to the group immunized with OVA (0.47%) or with OVA+TC (0.22%) (FIG. 10B).

As a whole, these results show that mice immunized with Omp19S+OVA by the nasal route presented an increase in the percentage of $CD4^+$ T lymphocytes but mainly of $CD8^+$ T lymphocytes producing IFN-$\gamma$ anti-OVA. This production was higher than the control group OVA immunized by the same route without adjuvants and even higher than the control group with a known adjuvant such as the cholera toxin.

Nasal co-administration of Omp16S induces the production of cytokines as a response to the Ag in spleen cell cultures. Results indicate that splenocytes from animals immunized nasally with OVA+Omp16S produced higher levels of IFN-$\gamma$ with respect to control animals (OVA) as a response to the antigen OVA (FIG. 11A). Co-administration of TC by the nasal route induced lower levels of IFN-$\gamma$ in the culture supernatants of splenocytes stimulated with OVA with respect to the group immunized with OVA+Omp16S. On the contrary, stimulation with OVA did not induce the secretion of IL-4 in the splenocytes of any of the studied groups in response to the antigen (FIG. 11B).

As for IL-10, a slight increase was detected with respect to the negative control, only in the group immunized with OVA+TC (FIG. 11C). Thus, Omp16S as adjuvant administered by the nasal route generates a Th1-type response.

In mice immunized with OVA+Omp16S by the nasal route there was an increase in the percentage of $CD4^+$ T lymphocytes but also of $CD8^+$ T lymphocytes anti-OVA producing IFN-$\gamma$ 3 weeks post-last immunization. This production was higher than the control group OVA immunized by the same route without adjuvant and even higher than the control group OVA+TC (FIGS. 12 A and B).

Immunization with Omp16S as nasal adjuvant induced the production of IFN-$\gamma$-producing antigen-specific $CD4^+$ T cells (0.97%) while the group immunized with TC as adjuvant did not induce a production different than the group immunized with OVA without adjuvant (OVA+TC 0.23% vs OVA 0.28%). However, induction in $CD8^+$ T lymphocytes was even higher. It may be observed a significant increase in the group OVA+Omp16S (1.08%) with respect to the group immunized with OVA (0.47%) or with OVA+TC (0.22%) (FIGS. 12 A and B). Finally, these results indicate that Omp16S as a nasal adjuvant induces the production of memory $CD4^+$ and $CD8^+$ T cells producing IFN-$\gamma$ in response to antigen (OVA).

The use of Omp19S and Omp16S as adjuvants by the nasal route induce (i) the release of Th1 cytokines as a response to the antigen and (ii) memory IFN-$\gamma$-producing antigen-specific $CD4^+$ and $CD8^+$ T lymphocytes.

These IFN-$\gamma$-producing T cells are indispensable for the generation of efficient immune responses against infections by pathogens having an intracellular phase in their life cycle (or when the pathogen is internalized by macrophages) such as virus, bacteria, parasites and fungi; or tumors. The fact that the adjuvants of the invention induce the production of this cytokine by the T lymphocytes could be beneficial for the development of vaccines against these type of diseases.

As a whole, these results show that the administration of Omp19S or Omp16S as adjuvants by the oral or nasal routes induces the production of memory $CD4^+$ and $CD8^+$ T lymphocytes which, upon encountering their specific Ag would produce IFN-$\gamma$, a very relevant quality for a mucosal adjuvant or immunomodulator.

Assays Using Parenteral Omp19S or Omp16S:

The humoral response was studied determining the titer of total IgG immunoglobulins and the profile of induced isotypes (IgG1 and IgG2a) against OVA when co-immunized with Omp19S as compared with the immunization of OVA in physiologic solution (SF) or OVA in CFA. The titers of total IgG were determined in the sera of animals obtained 3 weeks after the last immunization in the different groups by indirect ELISA. The results obtained showed that there were no significant increase of specific antibodies with respect to the immunization with OVA without adjuvant (FIG. 13), which would indicate that Omp19S has no effect on the magnitude of the triggered humoral response, whereas immunization with the positive control Complete Freund Adjuvant (CFA) generates an increase in the production of specific antibodies as expected. Omp19S as adjuvant has no effect on the magnitude of the humoral response.

When analyzing the profile of anti-OVA IgG isotypes in the immunized animals, it can be appreciated that the inoculation with OVA alone or using CFA as adjuvant induces a strong predominance of IgG1 antibodies, while using Omp19S as adjuvant this does not occur (ratio IgG1/IgG2a close to one) (FIG. 14). It is known that an immune response of the Th1 type is associated with an IgG2a antibody predominance over IgG1, while in the case of a Th2 response, this ratio is inverted (Crameri and Rhyner. Novel vaccines and adjuvants for allergen-specific immunotherapy. Curr Opin Immunol. 18 (6):761-8. 2006).

Therefore, although the immunization with Omp19S as adjuvant does not seem to have an effect on the magnitude of the humoral response, it does have an effect on the profile of induced specific isotypes, observing decrease in the ratio IgG1/IgG2a, which is associated with decrease of the IgG1 antibodies characteristic of a Th2 response. This inversion in the IgG1 predominance shows that, when using Omp19S as adjuvant, the production of Th2-type antibodies generated by the immunization with OVA is decreased, these results indicate that the adjuvants of the invention may be used to redirect Th2-type lymphocytic responses towards a Th1-type response, this effect could serve for reverting the conditions associated with allergic processes by re-directing a Th2 allergen-specific response towards a Th1 modulatory response.

The local reaction generated when BALB/c mice are inoculated subcutaneously with OVA together with Omp19S or CFA was analyzed. Local toxicity was determined by macroscopic alterations of the subcutaneous tissue. In the animals inoculated with Omp19S together with the OVA antigen there are no tissue signs of toxicity at the site of administration, given that no alterations were observed in the tissue when compared with the non-injected zone.

While in the animals inoculated with the complete Freund adjuvant, there was a granulomatose reaction at the site of inoculation, given by the formation of macrophagic granulomas characteristic of the use of this adjuvant (FIG. 15). CFA has a depot-type mechanism of action, insolubilyzing the antigen at the site of injection, which favors accumulation of macrophages together with other cells, which form the characteristic macrophagic granulomas evidencing signs of toxicity. The preparation of Omp19S used in all immunizations is soluble, thus it does not originate the formation of granulomas, which suggests a mechanism of action other than that of CFA. Immunization with Omp19S as adjuvant does not generate adverse local reactions in the subcutaneous tissue.

In order to analyze the T cell response in vivo, the DTH response induced by the OVA injection was evaluated in mice subcutaneously immunized with: (i) OVA, (ii) OVA+Omp19S, (iii) OVA+Omp16S, (iv) OVA+CFA, or (v) physiological solution (SF). To this end, OVA (20 µg) was injected in the footpad in one of the legs of immunized mice and SF was injected in the foodpad of the other leg as a control. Those animals immunized with OVA+Omp19S or +Omp16S presented increase in the footpad skin with respect to those animals immunized with OVA without adjuvant at 48 h and 72 h post-OVA injection (FIG. 16). As a whole, these results show that Omp19S and Omp16S are capable of inducing a T cellular response in vivo similar to that generated with an experimental known adjuvant such as CFA but without the adverse effects shown by this powerful adjuvant.

In order to evaluate the induced cellular immune response, the in vitro capacity to proliferate of splenocytes derived from animals as a response to the antigen was determined. Splenocytes were cultured in the presence of different concentrations of OVA or complete medium. After 5 days a $^3$H-tymidine pulse was given for 18 h and the incorporated radioactivity was measured. The results show that co-administration of OVA with Omp19S generates an increase of the proliferative response of cells from these mice in comparison with that from animals immunized only with OVA (FIG. 17). Both the stimulation with ConA (results not shown) and the positive control (CFA) produced significant increase in cell proliferation. These results indicate that the use of Omp19S as adjuvant has an effect on the generation of an efficient adaptive response evidenced by increase in the proliferative capacity of specific T cells.

For the determination of the type of anti-OVA T helper response induced by Omp19S as adjuvant administered parenterally, splenocytes of immunized mice were cultured in the presence of different concentrations of OVA or complete medium for 72 h and afterwards the pattern of cytokines secreted in the supernatants of these cells was analyzed. Capture ELISAs were performed using specific monoclonal antibodies for the detection of IFN-$\gamma$, IL-10, IL-4 and IL-17 in the culture supernatants of stimulated and control splenocytes.

Results indicate that the cells of animals immunized with OVA+Omp19S secreted significant amounts of IFN-$\gamma$ with respect to control animals (SF) and those immunized with OVA without adjuvant (FIG. 18), and secretion of this cytokine was antigen-specific and dose-dependent. The positive control (CFA) also induced the production of levels of this cytokine. Omp19S as parenteral adjuvant generates a Th1-type response.

In contrast to this, the levels of IL-4 produced showed no significant differences in the various groups; although there was an increase of such cytokine in response to stimulation with OVA as compared with SF group cells, levels were similar in the animals inoculated only with OVA, OVA+Omp19S and OVA+CFA (FIG. 19A). Similarly, the production of IL-10 in spleen cells does not present differences between the various groups, though there is an increase with respect to the SF group in all cases (FIG. 19B). This would indicate that the antigen-specific production of IL-4 and IL-10 does not result from the adjuvants, being characteristic of this antigen instead. Stimulation with the mitogen control (ConA) produced significant levels of all the cytokines under analysis. Based on these results, the cytokine pattern shown suggests that the response triggered by immunization with Omp19S as adjuvant corresponds to a Th1 profile, there being increased production of IFN-γ but not of IL-4 and IL-10.

Antigen specific IFN-γ producing T cells are indispensable for generating effective immune responses against pathogen infections with some intracellular phase in its life cycle (or when the pathogen is internalized by macrophages) such as virus, bacteria, parasites and fungi; or tumors. The fact that the adjuvant induces the production of these cytokines via T lymphocytes could be beneficial for the development of vaccines against such type of diseases. Since the adjuvants of the invention induce Th1 responses, they may be used in vaccine preparations against such pathogens.

After analyzing the response of Th1 and Th2 lymphocytes and to further characterize the type of immune response, the contribution of Th17 cell population in the response triggered was evaluated. For such purpose, levels of IL-17 produced in response to stimulus in the culture supernatants were measured (FIG. 20). The results indicated that after immunization with Omp19S+OVA, a dose-dependent Th17 response is generated upon in vitro stimulation with the antigen.

The analysis of the immune responses of $CD8^+$ T cells in normal animals is restricted by the low frequency of such cells that respond to a particular epitope. Transgenic mice for the T receptor have been used experimentally as a source of T cells with defined specificity. One of the most widely used models are OT-1 transgenic mice, in which $CD8^+$ T cells express the specific T receptor for OVA SIINFEKL peptide (SEQ ID NO: 11) presented in the context of MHC I co-stimulatory molecules ($H-2K^b$) (Harmala, Ingulli, Curtsinger, Lucido, Schmidt, Weigel, Blazar, Mescher and Pennell. The adjuvant effects of *Mycobacterium tuberculosis* heat shock protein 70 result from the rapid and prolonged activation of antigen-specific CD8+ T cells in vivo. J Immunol. 169 (10):5622-9. 2002).

Such mice were used for in vivo analysis of $CD8^+$ adaptive immune T response against the antigen.

In order to characterize the specific $CD8^+$ T response in the presence or absence of the adjuvants of the invention CFSE stained spleen and lymph node cells from OT-1 mice were adoptive transferred intravenously into C57BL/6 mice. One day after the adoptive transfer the mice were inoculated s.c. with OVA in conjunction with the adjuvants Omp19S, Omp19S PK (Omp19S treated with proteinase K), lipopolysaccharide (LPS) or SF. Five days later the number of OT-1 cell marked with CFSE was analyzed in the spleen and draining lymph nodes of immunized mice by flow cytometry.

In control animals inoculated with SF, lower percentages of cell division of specific $CD8^+$ cells stained with CFSE were observed. Animals immunized with OVA+Omp19S adjuvant showed a higher ratio of cells that underwent more than one division as compared with mice immunized with OVA without adjuvant, in both spleen (FIG. 21) and in lymph nodes (FIG. 21).

As regards spleen, the group immunized with SF showed proliferation value of (21.79%), whereas in the group immunized with OVA without adjuvant the percentage of cells that divided (75.01%) was lower than in the group of mice immunized with Omp19S as adjuvant (86.44%). A similar result was found for draining lymph node cells. In order to control that the effect on the response effectively results from the adjuvant and not from some non-protein contaminant such as LPS, animals were immunized with the adjuvant in degraded form. It was observed that immunization with the adjuvant degraded with proteinase K induced proliferation levels similar to inoculation with OVA without any adjuvant. OT-1 cells from animals immunized with positive control (LPS) showed proliferation levels similar to those in the group immunized with Omp19S as adjuvant.

These results indicate that immunization with Omp19S as adjuvant induces increased activation of OVA-specific $CD8^+$ T cells thus increasing their proliferative capacity, demonstrating the generation of efficient $CD8^+$ adaptive immune T response against the antigen.

After observing that there is an efficient antigen-specific $CD8^+$ T cell response induced by the adjuvant of the invention, it was evaluated whether these $CD8^+$ cells were capable of inducing significant levels of IFN-γ, characteristic of a T helper 1-type response. For such purpose, C57BL/6 mice were immunized with: (i) OVA; (ii) OVA+Omp19S, or (iii) OVA+Omp19S PK by s.c. route. Seven days later, spleens were removed from the animals. Splenocytes were stimulated with culture medium, 500 µg/ml OVA+5 µg/ml SIINFEKL peptide (SEQ ID NO: 11)+APC MO5 or Pma-Ionomycin and the intracellular IFN-γ production was measured by flow cytometry.

The population of IFN-γ-producing $CD8^+$ T cells was greater in mice immunized with Omp19S as OVA adjuvant (0.73%) in in vitro stimulation with OVA as compared to cells from animals immunized only with OVA, in which the frequency of IFN-γ-producing $CD8^+$ cells (0.14%) was similar to the isotype control. These results indicate that the polypeptide used as adjuvant induces the differentiation of $CD8^+$ T cells able to produce IFN-γ in response to antigen stimulation (FIG. 22). Indeed, it was observed that immunization of mice with the degraded protein (Omp19S PK) the frequency of cells expressing such cytokine is similar to the cells from the group immunized with OVA without adjuvant (0.15%); this result confirms that the adjuvant effect is derived from the adjuvant polypeptide. In all cases, isotype controls showed similar values.

These results indicate that Omp19S is capable of inducing the production of $CD8^+$ T lymphocytes that secrete IFN-γ in response to the antigen. These IFN-γ producing $CD8^+$T cells are indispensable for generating effective immune responses against infection by pathogens with some intracellular phase in their life cycle such as virus, bacteria, parasites and fungi; or tumors. The fact that the adjuvant induces such cytokine production by T lymphocytes may be beneficial for the development of vaccines against such type of diseases.

Since activation and production of IFN-γ by $CD8^+$ cells in response to OVA antigen was observed in mice immunized with the adjuvants of the invention, it was further investigated whether after immunization of animals with the adjuvants of the invention Ag-specific cytotoxic cells were induced. For such purpose, C57BL/6 mice were immunized by s.c. route, and 3 weeks later an in vitro cytotoxicity assay was conducted, wherein target cells (OVA-expressing MO5 or non-expressing-OVA B16) were marked with $^{51}Cr$ and then incubated with splenocytes from the immunized mice (effector cells). The release of $^{51}Cr$ by target cells was measured in the supernatants. As shown in FIG. 23, splenocytes from animals immunized with Omp19S or Omp16S as adjuvants induced a higher percentage of lysis as compared to such cells from the group immunized with OVA without adjuvant. Complete Freund's adjuvant (CFA) was used as positive control. Omp19S and Omp16S as adjuvants induce in splenocytes from immunized mice a greater cytotoxic response than the response induced by adjuvant CFA and with no signs of alterations in the immunized tissue or other adverse effects.

Omp19S and Omp16S polypeptides have proven to be useful in vaccine formulations comprising any immunogen or antigen which adjuvant is at least Omp19S and/or Omp16S. The polypeptides of the invention are useful adjuvants for generating Th1, Th17 and cytotoxic responses in mucosa by the use thereof both nasally and orally, and systemic route after parenteral administration.

T cell immune responses are considered protective against pathogens and tumors. The adjuvants of the invention induce IFN-γ-producing T responses when administered by parenteral and mucosal (nasal and oral) routes, and thus might be useful in vaccine preparations against infections by pathogens with some intracellular phase in its life cycle (or when the pathogen is internalized by macrophages) as virus, bacteria, parasites and fungi; or tumors. They also induce cytotoxicity against a tumor cell line that expresses the antigen (MO5), and thus could be used in vaccines against tumors.

Also, since Th1 cytokines usually inhibit Th2 cytokines, it is intended to induce Th1 responses against an allergen in anti-allergic vaccines, so as to re-direct an allergen-specific Th2 response towards a modulatory Th1 response. The adjuvants of the invention may be useful in modulating the response to allergens.

Recent evidence has demonstrated a critical role of IL-17 producing T cells in vaccine-induced protection in infections by intracellular and extracellular pathogens. The generation of Th1 and Th17 responses has been reported in vaccines against *Bordetella pertussis*, wherein the population of Th17 cells is important for the effectiveness of the protection. It has also been shown that IL-17 has an important role in protection against *Streptococcus pneumoniae* and *Mycobacterium tuberculosis*. The mechanism proposed for the efficacy of vaccines inducing Th17 cell activation is by regulation of chemokines. In this sense, using an adjuvant capable of inducing the production of this cytokine would be beneficial in vaccines against such type of pathogens.

Finally, the adjuvants of the invention could be used as immunomodulators or activators of immune response in various pathologies where the immune response is involved.

As shown in FIG. 24 and given that the expression of α4β7 directs lymphocytes to effector mucosal sites (intestinal lamina propria), these results show that Omp19S orally administered as adjuvant of tetanus toxoid (TT) in a vaccine formulation induces migration of CD4+ and CD8+ effector T lymphocytes to the intestinal mucosa (small intestine lamina propria).

The Omp16S and Omp19S adjuvant polypeptides may also be expressed in situ, being administered as vectors to DNA or RNA. As shown in FIG. 25, Omp16 and Omp19 proteins are correctly expressed after transfection of eukaryotic cells with pCI-Omp16S or pCI-Omp19S plasmids, respectively. This result indicates that such proteins may be produced by eukaryotic cells, administering expression vectors to eukaryotic cells or greater organisms (vertebrate or mammalian) such that the adjuvant is expressed in situ and exerts its effect.

Further characterizing the mechanism whereby the effect of the adjuvants of the present invention occurs, assays were conducted where stomach extract supernatants were co-incubated with Omp19S polypeptides and then BODIPY FL casein or BODIPY FL OVA was added (intramolecularly marked antigens so that they do not fluoresce when non-degraded, but becoming fluorescent when degraded) to 100 µl NaHCO3 buffer. It was observed that the presence of the polypeptide Omp19S reduces the degradation of the antigen, similar effect to that observed when using a mammal protease inhibitor cocktail (as a control that the stomach enzymatic activity can be inhibited). As mentioned above, it is observed that the action of the adjuvant of the present invention further comprises a mechanism inhibiting protease action, thus leading to increased antigen half life (FIG. 26).

These results indicate that immunization using Omp19S adjuvant, in addition to inducing a higher immune response, decreases antigen degradation, so that the amount of Ag administered in vaccines to stimulate and maintain immune response could be decreased.

Additional assays performed to analyze protease inhibitory action by adjuvant polypeptides of the present invention, were aimed at evaluating whether Omp19S polypeptide is capable of inhibiting degradation of different antigens by proteases from the stomach of BALB/c mice, both eukaryotic (BSA, OVA) and bacterial (BLS, SurA, DnaK), without limiting the scope of the present invention. Each antigen was treated with: (i) stomach extract supernatant; (ii) stomach extract supernatant and Omp19S; (iii) stomach extract supernatant and mammal protease inhibitor cocktail (as a control that the stomach enzymatic activity can be inhibited). These reaction mixtures were subjected to sodium dodecyl sulphate polyacrylamide gel electrophoresis (SDS-PAGE) and then to Coomassie blue staining (FIG. 27). These assays demonstrate that the adjuvant polypeptides of the present invention have inhibitory activity of antigen degradation, both from eukaryotic and bacterial origin.

In order to test the antigen degradation inhibitory action by stomach proteases an in vivo assay was carried out, using BODIPY FL casein as antigen model. BALB/c mice were inoculated orally with: (i) NaHCO3 buffer (1 M, pH8) (Vehicle), (ii) BODIPY FL casein with Omp19S (iii) BODIPY FL casein with aprotinin (a known protease inhibitor); (iv) BODIPY FL casein. After a reaction time, mice were sacrificed and the extracts were analyzed by fluorescence emission, observing inhibition of antigen degradation by stomach proteases in vivo (FIG. 28).

Based on the different assays wherein the inhibitory capacity of antigen degradation by stomach proteases was determined, at least 30% inhibitory effect of the action of such proteases is observed, preferably at least 50%. Among proteases inhibited by the action of the adjuvants of the present invention are serine proteases, aspartyl proteases, metalloproteases and cysteine proteases.

The adjuvant polypeptides of the present invention are ideal since the capacity to inhibit the destruction of Ag by proteases increases the half-life thereof and improves the induction of an immune response. This could mean that smaller amount of Ag would be required to induce the same immune response, thus reducing vaccines costs.

Therefore, it is surprising that Omp16S and Omp19S act as highly efficient adjuvants for antigens that are not related to *Brucella* antigens.

This invention is better illustrated according to the following examples, which are not to be construed as a limitation on the scope thereof. In contrast, it should be clearly understood that other embodiments, modifications and equivalents thereof can be applied, which upon reading the present specification can be suggested by those skilled in the art without departing from the spirit of the present invention and/or scope of the appended claims.

EXAMPLES

Example 1

Cloning, Expression and Characterization of Brucella abortus Omp16S and Omp19S Polypeptides Omp19S polypeptide was cloned without the consensus lipidation sequence in vector pET22+ with the addition of a histidine tail at the carboxyl-terminal end (Novagen, Madison, Wis., USA), as described in (Giambartolomei, Zwerdling, Cassataro, Bruno, Fossati and Philipp. Lipoproteins, not lipopolysaccharide, are the key Mediators of the proinflammatory response elicited by heat-killed Brucella abortus. J Immunol. 173 (7):4635-42. 2004). In further detail, specific oligonucleotides were designed containing the restriction sites for NdeI and XhoI enzymes at the 5' end, and region 3' of Omp19 gene without the amino terminal end corresponding to the signal peptide sequence and the amino terminal cysteine:

```
Omp19
                                         (SEQ ID No: 3)
Sense:         5'CTGGCCATATGCAGAGCTCCCG3'

(SEQ ID No: 4)
Antisense:     5'AAACTCGAGGCGCGACAGCGTCAC3'
```

In the PCR reaction, the genomic DNA from B. abortus 544 was used as template. The product of the ligation reaction was used to transform competent bacteria of the JM109 strain and plasmid DNA was purified using a commercial kit (Promega).

With this construct, competent cells of E. coli BL21 (DE3) (Stratagene, La Jolla, Calif., USA) were transformed and the protein expression was induced with isopropyl-β-D-thiogalactopyranoside (IPTG). The bacterial extract was sonicated and the protein was purified by affinity chromatography using nickel columns (Qiagen, Germany), thus obtaining the purified non-lipidated polypeptide (Omp19S) (SEQ ID No: 1).

Omp16S polypeptide was cloned without the consensus lipidation sequence in vector pET22+ with the addition of a histidine tail at the carboxyl-terminal end (Novagen, Madison, Wis., USA), as described in (Giambartolomei et al. Lipoproteins, not lipopolysaccharide, are the key Mediators of the proinflammatory response elicited by heat-killed Brucella abortus. J Immunol. 173 (7):4635-42. 2004). In further detail, specific oligonucleotides were designed containing the restriction sites for NdeI and XhoI enzymes at the 5' end, and region 3' of Omp16 gene without the amino terminal end corresponding to the signal peptide sequence and the amino terminal cysteine:

```
Omp16
                                         (SEQ ID No: 5)
Sense:         5'GTTGCCATATGGCGTCAAAGAA3'

(SEQ ID No: 6)
Antisense:     5'TTGCCGCTCGAGCCGTCCGGCCCC3'
```

In the PCR reaction, the genomic DNA from B. abortus 544 was used as template. The product of the ligation reaction was used to transform competent bacteria of the JM109 strain and plasmid DNA was purified using a commercial kit (Promega).

With this construct, competent cells of E. coli BL21 (DE3) (Stratagene, La Jolla, Calif., USA) were transformed and the protein expression was induced with isopropyl-β-D-thiogalactopyranoside (IPTG). The bacterial extract was sonicated and the protein was purified by affinity chromatography using nickel columns (Qiagen, Germany), thus obtaining the purified non-lipidated polypeptide (Omp16S) (SEQ ID No: 2).

Non-lipidated polypeptides Omp19S and Omp16S were subjected to sodium dodecyl sulphate polyacrylamide gel electrophoresis (SDS-PAGE), followed by Coomassie blue staining to monitor the various purification stages. The identity thereof was confirmed by Western Blot using an anti-Omp19 and other anti-Omp16 monoclonal antibody.

The possible traces of LPS that could contaminate the purified polypeptides were removed using Polymyxin B sepharose resin (Sigma-Aldrich). Then, an assay with Limulus Amebocyte kit (Associates of Cape Cod, Woods Hole, Mass.) was performed to determine the amount of LPS present therein. In all the experiments described in this application, preparations of purified recombinant polypeptides containing <0.25 U endotoxin/µg polypeptide were used.

Omp19S and Omp16S concentration was assessed using the bicinchoninic acid method (Pierce, Rockford, Ill.) using bovine serum albumin (BSA) as a standard. The purified polypeptides were aliquoted and stored at −70° C. until use.

Example 2

Animal Immunization Assays Using Omp19S and Omp16S as Adjuvant

LPS-free purified bovine Ovalbumin (OVA) (Sigma-Aldrich) was used as model antigen.

6 to 8 week-old female mice of the strain BALB/c ($H-2^d$) or C57BL/6 ($H-2^b$) were used. They were obtained from the Universidad Nacional de La Plata and were kept in animal housing facilities of Instituto de Estudios de la Inmunidad Humoral (IDEHU). They received food and water ad libitum.

Three types of immunization were performed: oral, nasal and parenteral.

—Oral Immunization:

For oral immunization, two protocols were followed, wherein the injection routine of different groups of mice was varied. Both immunization routines assayed gave similar results.

Routine 1:

| Immun. #1 | Immun. #2 & 3 | Immun. #4 & 5 | Immun. #6 | Sacrifice |
|---|---|---|---|---|
| 0 | 7  8 | 14  15 | 21 | |
| ↓ | ↓  ↓ | ↓  ↓ | ↓ | ↓ |

In this first routine, BALB/c mice were immunized orally six times on day 0, 7, 8, 14, 15 and 21 with (i) 100 µg OVA; (ii) 100 µg OVA+100 µg Omp19S; (iii) 100 µg OVA+100 µg Omp16S; (iv) 100 µg OVA+10 µg cholera toxin (CT, Sigma) embedded in $NaHCO_3$ buffer (1M, pH8). Two weeks after the last immunization (day 35), the mice were sacrificed to evaluate the cellular immune response.

Routine 2:

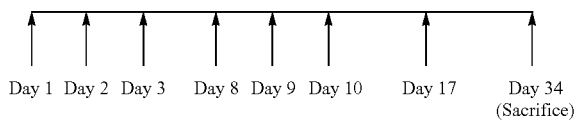

Day 1 Day 2 Day 3  Day 8 Day 9 Day 10   Day 17   Day 34
(Sacrifice)

BALB/c mice were immunized orally six times on day 1, 2, 3, 8, 9 and 10 with (i) 100 μg OVA; (ii) 100 μg OVA+150 μg Omp19S; (iii) 100 μg OVA+150 μg Omp16S; (iv) 100 μg OVA+5 μg cholera toxin (CT, Sigma) embedded in $NaHCO_3$ buffer (1M, pH8). A week after the last immunization (day 17), a delayed-type hypersensitivity (DTH) response test was performed, and three weeks after the last immunization (day 34), animals were sacrificed to evaluate the cellular immune response.

—Nasal Immunization:

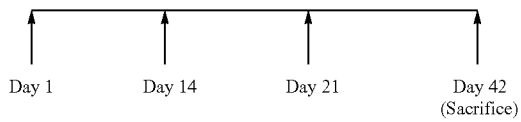

Day 1         Day 14        Day 21        Day 42
(Sacrifice)

C57BL/6 mice were immunized nasally three times every 7 days with (i) 50 μg OVA; (ii) 50 μg OVA+10 μg Omp19S; (iii) 50 μg OVA+10 μg Omp16S; (iv) 50 μg OVA+1 μg cholera toxin (CT, Sigma). 12.5 μl were injected per nostril. Three weeks after the last immunization, animals were sacrificed to evaluate the cellular immune response.

The animals were bled by submaxilar route and sera were stored at −20° C. for detecting specific Abs.

—Parenteral Immunization:

The animals were immunized via subcutaneous (s.c) route three times every 7 days with (i) 100 μg OVA; (ii) 100 μg OVA+100 μg Omp19S; (iii) 100 μg OVA+100 μl CFA (Sigma-Aldrich) or (iv) SF. Three weeks after the last immunization, the animals were bled to obtain the sera, and some of them (5 per group) were sacrificed to evaluate the cellular response and others were subjected to DTH (5 per group).

Example 3

Test for Assessment of Omp19S and Omp16S Activity

Delayed-Type Hypersensitivity Response (DTH):

Seven days after the last immunization, the mice were inoculated by intradermal route in the right footpad with 20 μg OVA and with physiological solution (SF) in the left footpad. Response was evaluated by measuring the right footpad skin fold increase compared to the left one, using a digital caliber of 0.01 mm precision, 48 h and 72 h after inoculation.

Obtaining Mice Splenocytes:

Mice anesthetized with ether, were bled white by the retro-orbital plexus and sacrificed by cervical dislocation. An appropriate incision was performed, opening the peritoneal cavity, to exteriorize the spleen, which was extracted with forceps and scissors under aseptic conditions. Spleen was grinded into small fragments using curved tip scissors. 3 ml RPMI 1640 (Gibco) was added and it was homogenized. The suspension was brought to 8 ml and filtered through steel mesh to retain the cellular and tissue debris. Then it was washed with RPMI 1640, and the cells were suspended in complete culture medium (RPMI 1640 with the addition of 10% fetal bovine serum (SFB, Gibco), 2 mM L-glutamine and pyruvate, 25 mM HEPES, 100 U/ml penicillin and 100 μg/ml streptomycin).

Obtaining Lymphocytes from Mice Mesenteric Lymphatic Nodes:

Mice anesthetized with ether, were bled white by the retro-orbital plexus and sacrificed by cervical dislocation. An appropriate incision was performed, opening the peritoneal cavity, to exteriorize mesenteric lymph nodes, which were extracted with forceps and scissors under aseptic conditions. They were then incubated with collagenase (2.5 mg/ml) for 30 minutes. Collagenase was then removed and lymph nodes were grinded into small fragments using curved tip scissors. After addition of 3 ml RPMI 1640 (Gibco) the cell suspension was homogenized, brought to 8 ml and filtered through steel mesh to retain the cellular and tissue debris. Then it was washed with RPMI 1640, and the cells were resuspended in complete culture medium (RPMI 1640 with the addition of 10% fetal bovine serum (SFB, Gibco), 2 mM L-glutamine and pyruvate, 25 mM HEPES, 100 U/ml penicillin and 100 μg/ml streptomycin).

Viable Cell Count:

To determine the number of viable cells, the Trypan Blue Exclusion method was used. 0.2% Trypan Blue solution was prepared in PBS. 50 μl of the suspension to be counted was taken and 50 μl Trypan Blue solution was added. It was loaded into a Neubauer chamber and the number of viable cells was determined by optical microscope.

Cell Stimulation:

Splenocytes ($4 \times 10^6$ cells/ml) from immunized mice were cultured in the presence of OVA (100 and 1000 μg/ml), complete medium, or control mitogen (Concanavalin A, 5 μg/ml) in 48-well plates. Cultures were performed in a stove at 37° C. in atmosphere of 5% $CO_2$ for 72 hours for experiments using cells from BALB/c mice or for 5 days for experiments using cells from C57BL/6 mice. Supernatants from these cells were used for determination of secreted cytokine by ELISA.

Capture ELISA for Detecting Cytokines:

Capture ELISAs were performed using specific monoclonal Abs for detecting IFN-γ, IL-2, IL-10, IL-4 (OptEIA™, PharMingen, San Diego, USA) and IL-17 (Mouse IL-17 Quantikine, R&D Systems, Inc., Minneapolis, USA) in the culture supernatants of stimulated and control splenocytes. The protocol was performed according to manufacturer's instructions.

In Vitro Proliferation Assay:

Splenocytes from immunized mice ($2 \times 10^5$ cells/nil) were cultured in triplicates in the presence of OVA (100 and 1000 μg/ml), complete medium, or control mitogen (Concanavalin A, 5 μg/ml) in 96-well plates. The cultures were performed in a stove at 37° C. in atmosphere of 5% $CO_2$. Five days later a pulse of titrium-labeled thymidine (1 μCi/well) was added and 18 h. later cells were harvested, and radioactive thymidine incorporation (expressed in counts per minute: cpm) was measured with a beta counter. The results were expressed as stimulation index SI (cpmOVA/cpm-RPMI). When a SI is >2, it is considered to be significant.

Determination of Intracellular IFN-γ in $CD4^+$ and $CD8^+$ T Lymphocytes:

—Antigen-presenting cells (APC) MO5 and A20J

A20J cells were grown (mouse B lymphoma, syngeneic for BALB/c, ATCC TIB208) in complete culture medium (RPMI 1640 with the addition of 10% fetal bovine serum (SFB, Gibco), 2 mM L-glutamine and pyruvate, 25 mM HEPES, 100 U/ml penicillin and 100 µg/ml streptomycin) for two days. These cells were stimulated with OVA 10 µg/ml one day before the trial, herein after referred to as A20JOVA. Similarly, MO5 cells (syngeneic B16 melanoma cells for C57BL6 and stably transfected with an OVA-expressing plasmid) were grown in order to use them as OVA-presenting cells, in complete medium supplemented with 1 mg/ml geneticin.

Microscopy showed that the state and the number of cells were optimal for use. These cells were treated with Mitomycin C (25 µg/ml, Sigma) at 37° C. for 30 min., washed 3 times with RPMI and suspended in complete culture medium.

—Splenocytes from Mouse Spleen

Pooled mouse splenocytes from each immunization group were cultured in T25 bottles, in complete culture medium. On the next day they were cultured in a 6-well plate $8 \times 10^6$ cells/ml, in 1 ml complete medium supplemented with recombinant IL-2 (10 U/ml). Subsequently, the stimuli listed below were added.

—Stimuli

For each group of immunized mice, the following stimuli were conducted:

(a) Negative control: complete culture medium with the addition of mouse recombinant IL-2 (10 U/ml) (PeproTech. Inc., Rocky Hill, USA)

(b) Antigenic stimulus i—In the case of BALB/c animals, OVA 500 µg/ml+MHC class II-restricted OVA peptide $OVA_{323-339}$ KISQAVHAAHAEINEAGOVA ISQAVHAAHAEINEAGR (SEQ ID NO: 12) (1 µg/ml)+ A20JOVA cells treated with mitomycin in a ratio of 25 splenocytes:1 APC were used, all suspended in 1 ml complete culture medium supplemented with recombinant IL-2.

ii—In the case of C57BL/6 animals, OVA 500 µg/ml+ OVA peptide$_{257-264}$ SIINFEKL (SEQ ID NO: 11) restricted to MHC-I (0.5 µg/ml)+MO5-presenting cells in a ratio of 25 splenocytes:1 APC were used, all suspended in 1 ml complete culture medium supplemented with recombinant IL-2.

c) Positive control, mitogenic stimulation. PMA 20 ng/ml+Iono 0.75 µg/ml, both suspended in 1 ml complete culture medium supplemented with recombinant IL-2.

After 18-h incubation with the different stimuli, 10 µg/ml Brefeldin A (Sigma) was added to each well stimuli and incubated additionally for 6 h. Afterwards splenocytes were collected and separated into two tubes (one for isotype control and one for staining with IFN-γ) for subsequent staining with antibodies for cytometry tests.

—Cellular Subtypes and IFN-γ Staining

Stimulated and control splenocytes were incubated for 30 min. at 4° C. with specific anti-CD4 mouse monoclonal Abs marked with PE-Cy5.5 and anti-CD8 mouse Ab marked with Alexa Fluor 647 (BD Biosciences, San Jose, Calif.). They were then washed with PBS and subsequently fixed by the treatment for 20 min. at room temperature with 4% paraformaldehyde solution. After washing with PBS cells were permeabilized by treatment with permeabilization buffer (2% saponin, 10% SFB in PBS) for 30 min. Cells thus permeabilized were centrifuged at 600 g for 5 min., and treated with a specific anti-mouse-IFN-γ Ab marked with PE for 30 min. For all treatments, marking was performed in parallel with Abs marked with the same fluorochromes but of irrelevant specificity as isotype controls. After washing, cells were suspended in PBS and finally analyzed using a flow cytometer (BD FACSCalibur) and FlowJo software (version 5.7.2)

Determination of α4β7 Protein on Mesenteric Lymph Node Lymphocytes:

After obtaining the cells from the mesenteric lymph nodes according to the protocol mentioned above, pools were assembled depending on the immunization group. $2 \times 10^6$ cells were taken from each of them, and were treated with anti-mouse-CD4 marked with FITC, anti-mouse-CD8 marked with PE-Cy5.5 and anti-mouse-α4β7 marked with PE (BD Biosciences, San Jose, Calif.). Subsequently, cells were fixed in 100 µl 4% paraformaldehyde, and then analyzed by flow cytometer (FACSCalibur BD) and FlowJo software (version 5.7.2).

Indirect Enzyme-Linked ImmunoSorbent Assay (ELISA) for Detecting Specific Abs:

To perform the ELISA, polystyrene plates (Maxisorp, NUNC, Denmark) were used. Plates were coated with 1 µg OVA per well and blocked with 200 µl of skim milk (Molico) at 3% in PBS buffer. Then the plates were incubated with serial dilutions of the sera and revealed with anti-mouse-IgG conjugated with HRP. To determine the specific isotypes, plates were incubated with specific antibodies for mouse Ig isotypes, IgG1 and IgG2a, conjugated with HRP (Santa Cruz). Incubations were performed for 1 h at room temperature. 1% skim milk powder, 0.05% Tween in PBS were used as diluent for sera and conjugate. After each incubation step, the plate was washed 3 times with 0.05% PBS-Tween. The ELISA was revealed with 2 mg/ml ortho-phenylenediamine and 0.03% $H_2O_2$ in 0.1M phosphate/citrate buffer. The reaction was stopped between 15 and 30 minutes of incubation with 50 ml $H_2SO_4$ 4N. Developed optical densities were determined at 492 nm in a microplate reader Metertech Σ960. To determine the antibody titer, 20 sera from normal mice were tested at a dilution $\frac{1}{100}$, establishing the cut-off value as the average value of the absorbance thereof plus three standard deviations. The antibody titer was calculated as the last dilution that was greater than the cut-off value.

Cytotoxicity Assay

Target Cells:

MO5 cells were used as target (B16 melanoma cells syngeneic with C57BL6 and stably transfected with an OVA-expressing plasmid) cultured in complete medium supplemented with 1 mg/ml geneticin. B16 cells were used as control (melanoma cells not transfected with OVA plasmid).

Stimulator Cells:

MO5 cells were used as stimulus cultured in complete medium supplemented with 1 mg/ml geneticin, which were pre-incubated with 10 µg OVA for 18 h and then treated with mitomycin C (25 µg/ml) at 37° C. for 30 min, washed 23 times with RPMI and suspended in complete medium.

Effector Cells:

Splenocytes from immunized and control mice were the effector cells ($2.5 \times 10^7$ total cells), previously stimulated for 5 days with the described stimulator cells ($0.5 \times 10^6$ cells) in complete medium+10 U/ml recombinant IL-2.

Labelling Target Cells:

Target cells were incubated with radioactive sodium chromate in aqueous solution ($^{51}$Cr, Amersham Biosciences) at a rate of $0.1$ mCi/$1 \times 10^6$ cells, for 1 h in a water bath at 37° C. and then washed 3 times with RPMI.

Assay:

Target cells were incubated with different amounts of effector cells (ratio 100:1, 50:1) for 6 hours in a stove at 37° C. Subsequently, 100 µl were harvested from the culture supernatants and radiation was quantified by a γ counter (Clinigamma, LKB, Wallac, Turku, Finland). The results obtained were converted into % lysis using the following formula:

$$\% \text{ lysis} = \frac{cpm_x + cpm_{LE}}{cpm_{max} - cpm_{LE}} \times 100$$

Wherein:
x: sample
LE: spontaneous release of target cells when incubated without effector cells
max: maximum release, determined incubating target cells with 1% Triton X-100.

Example 4

Experiments Showing the Omp19s Adjuvant Activity in Transgenic Mice

OT-1 strain mice, which CD8+ T cells express the specific T cell receptor for ovalbumin (OVA) peptide SIINFEKL, (SEQ ID NO: 11) were used as donor antigen-specific CD8+ T cells. These mice were purchased from Jackson Laboratory and brought to the country by Dr. Fernando Goldbaum, who has gently offered this strain. Singenic C57BL/6 mice acquired at the Universidad Nacional de La Plata were used as receptors of the cells from the OT-1 animals. All mice received water and food ad libitum and were maintained under pathogen-free conditions.

Purified and LPS-free ovalbumin (OVA) (Sigma-Aldrich) was used as model antigen as described in Example 1. In all the described experiments, preparations of purified recombinant polypeptides containing <0.25 U endotoxin/µg polypeptide were used.

In some experiments, the polypeptide was digested with proteinase K as a control. To this end, Omp19S was treated with proteinase K-agarose from tricirachium album (Sigma Aldrich) for 2 h at 37° C. following the manufacturer's instructions. Then, the resin was centrifuged and supernatants were incubated for 1 h at 60° C. with the purpose of inactivating any enzyme trace that might have solubilized. Then, digestion was checked using SDS-PAGE and subsequent Coomasie blue staining. The polypeptide thus treated (Omp19S PK) was used as a control of the adjuvant effect induced by said polypeptide.

Adoptive Transfer of OTI Mice Cells and Immunization:

OVA-specific CD8+ T cells were obtained from spleen and lymph nodes of OT-1 mice, which were purified by negative selection using the mouse CD8+ T lymphocyte Enrichment kit (BD Imag) and then stained with CFSE 5 µM at 37° C. for 15 minutes. The free carboxyfluorescein succinimidyl ester (CFSE) (Molecular Probes) was cooled down by adding phosphate buffer saline (PBS) 10% SFB. Later, the marked cells were washed with PBS and resuspended in a 0.1 ml volume. Then, the cells were injected intravenously (i.v.) in the lateral tail veins of the animals. One day later, animals were inoculated subcutaneously (s.c.) with: (i) OVA 60 µg, (ii) OVA 60 µg+Omp19S 100 µg, (iii) OVA 60 µg+Omp19S PK 100 µg, (iv) OVA+LPS (Sigma Aldrich) 10 µg as a control, or (v) PBS.

In Vivo Proliferation Assay:

Five days after immunization, animals receiving cells from OT-1 were sacrificed. The spleen and drining lymph nodes (inguinal and axillary) were extracted and the number of antigen-specific CD8+ T cells marked with CFSE was determined by flow cytometry (BD FACSAriall). The results were analyzed using the FlowJo software (Version 5.7.2).

Example 5

Omp19S as Adjuvant in Vaccine Formulations 6 immunizations via the oral route were performed with (i) TT (tetanus toxoid) 100 Lf, (ii) TT 100 LF+Omp19S 150 µg, or (iii) TT 100 Lf+TC 5 µg according to the following scheme:

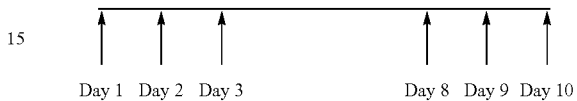

Day 1 Day 2 Day 3    Day 8 Day 9 Day 10

Mice were sacrificed 3 weeks after the last immunization and the percentage of T cells expressing the marker α4β7 was analyzed in mesenteric lymph nodes.

Example 6

Cloning of Omp16S- and Omp19S-Codifying Genes in an Eukaryote Expression Vector

Primer Design:

The primer oligonucleotides were designed from the nucleotide sequence of Omp16 and Omp19 (Genbank Omp16: ACCESSION L27996. Omp19: ACCESSION L27997). The primers contain XhoI and XbaI restriction sites (in bold). All "primers" were added the known efficient Kozak sequence for transcription in eukaryotes (underlined in the sequence).

```
Omp16S:
"Sense":
                                        (SEQ ID No: 7)
5' CTC CTC GAG ACC ACC ATG GCG TCA AAG AA 3'

"Antisense":
                                        (SEQ ID No: 8)
5' TTG TCT AGA TTA CCG TCC GGC CCC GTT GA 3'

Omp19S:
"Sense":
                                        (SEQ ID No: 9)
5' GGC ATT CTC GAG ACC ACC ATG CAG AGC TCC 3'

"Antisense":
                                        (SEQ ID No: 10)
5' TTT TCT AGA TCA GCG CGA CAG CGT CAC 3'
```

Cloning:

Genes of interest were amplified by polymerase chain reaction (PCR) using the corresponding primers with an annealing temperature of 55° C. and using Brucella genomic DNA as template. The vector pCI-Neo (Promega) was used for cloning Omp16S and Omp19S. This vector was digested with XhoI and XbaI and then purified by the phenol:chloroform method. The amplification products from the PCRs were digested with the corresponding restriction enzymes. All the amplification products from the PCRs were re-purified by Wizard PCR Preps (Promega, Madison, Wis. USA). The ligation reactions were carried out at 4° C. overnight in the presence of DNA T4 ligase enzyme (Promega), 1 µl digested plasmid (pCI) and 2 µl of the corresponding digested insert. Then, JM109 (Promega) E. coli competent cells were transformed using the Cl$_2$Ca method with 5 µl of the ligation reaction. Transformed bacteria were selected, grown at 37° C. in LB plates with ampicillin (25 µg/ml). In order to determine the colonies containing the plasmid with the proper insert, a screening was carried out using the "colony PCR" method.

In Vitro Expression:

Transient Transfection of COS-7 Cells

In order to evaluate the in vitro expression of the plasmids in eukaryote cells, COS-7 cells (ATCC, CRL1651, Rockville, Md., USA) were transfected using the liposome method with 2 µg of the following constructs: pCI-Omp16S, pCI-Omp19S, or the pCI vector (as a control) and 20 µl Lipofectamine (Gibco BRL, Gaithersburg, Md. USA) following the manufacturer's protocol.

Expression of Omp16S and Omp19S in COS-7 Cells

Expression of the plasmids was assessed 24 h and 48 h after transfection (transient expression) in total protein extracts. This was analyzed by Western Blot, using different monoclonal antibodies: anti-Omp16 or anti-Omp19 and revealed using a chemiluminescence ECL kit (Amersham Pharmacia, Uppsala, Sweden)

Example 7

Inhibition of Stomach Enzymatic Activity In Vitro

Fluorometric Assay:
Substrates:
BODIPY FL Bovine ovalbumin (OVA) and BODIPY FL Casein were used as model antigens. Both antigens are intramolecularly marked so that they do not fluoresce when non-degraded, but they do fluoresce when degraded (EnzChek® Protease Assay Kit *green fluorescence*, Molecular probes).

6- to 8-week-old female mice strain BALB/c (H-2d) were used. These were obtained from the vivarium at the Universidad Nacional de La Plata and were maintained at the vivarium from the Instituto de Estudios de la Inmunidad Humoral (IDEHU). They received water and food ad libitum.

Obtaining of Mice Stomachs

Mice were sacrificed by cervical dislocation. A proper incision was practiced, opening the peritoneal cavity, so as to exteriorize the stomach which was extracted with forceps and scissors under aseptic conditions.

Processing of Mice Stomachs

Stomachs were first disaggregated with clamps and scissors and the parts obtained were transferred to a potter and embedded in NaHCO3 buffer (1M, pH8) to complete disaggregation. The extracts obtained were centrifuged at 10,000×g and supernatants were used to perform the assay.

Assay:

Negative control: BODIPY FL Casein or BODIPY FL OVA (10 µg/ml) in NaHCO3 buffer (1M, pH8).

Assessment of Omp19S inhibitory activity: stomachs were co-incubated with Omp19S (100 µg/ml) for 30 min. and then with BODIPY FL Casein or BODIPY FL OVA in 100 µl NaHCO3 buffer.

Other Controls:

Stomach self-fluorescence: stomach in 100 µl NaHCO3 buffer.

Determination that stomach enzymatic activity may degrade Casein or OVA: stomachs were co-incubated with BODIPY FL Casein or BODIPY FL OVA (10 µg/ml) in 100 µl NaHCO3 buffer.

Determination that stomach enzymatic activity may be inhibited: stomachs were co-incubated with a mammal proteases inhibitor cocktail (Sigma) for 30 min. and then with BODIPY FL Casein or BODIPY FL OVA (10 µg/ml) in 100 µl NaHCO3 buffer.

Positive control: BODIPY FL Casein or BODIPY FL OVA (10 µg/ml) in NaHCO3 buffer (1M, pH8) treated with proteinase K (Sigma).

In order to evaluate the fluorescence levels the reaction mixtures were transferred to 96-well black/opaque plates (low self fluorescence) (Costar). Fluorescence emission was analyzed in a Victor3, Perkin Elmer, Waltham, Mass. plate reader.

Example 8

Degradation Inhibition of Different Eukaryotic or Bacterial Antigens by Stomach Enzymes Eukaryotic antigens: bovine ovalbumin (OVA), bovine serum albumin (BSA)

Bacterial antigens: recombinant *Brucella* lumazine synthase (BLS), recombinant *Brucella* chaperone (DnaK) and recombinant *Brucella* peptidyl-prolyl cis-trans isomerase (SurA).

Assay:

The following reaction mixtures were made and incubated for 1 hour at 37° C.:

(i) 5 µg of each antigen (OVA, BSA, BLS, DnaK or SurA)

(ii) 5 µg of each antigen (OVA, BSA, BLS, DnaK or SurA) with 0.1 µg of stomach extract supernatant.

(iii) 5 µg of each antigen (OVA, BSA, BLS, DnaK or SurA) with 0.1 µg of stomach extract supernatant and 0.3 µg Omp19S.

(iv) 5 µg of each antigen (OVA, BSA, BLS, DnaK or SurA) with 0.1 µg of stomach extract supernatant and mammal proteases inhibitor cocktail (Sigma).

After incubation, each reaction mixture was subjected to a sodium dodecyl sulfate polyacrylamide gel electrophoresis (SDS-PAGE) and subsequent Coomasie blue staining.

Example 9

Co-Administration of Omp19S Inhibits Antigen Degradation by Stomach Proteases In Vivo BODIPY FL Casein (EnzChek® Protease Assay Kit *green fluorescence*, Molecular probes) was used as model antigen.

6- to 8-week-old female mice strain BALB/c (H-2d) were used. These were obtained from the vivarium at the Universidad Nacional de La Plata and were maintained at the vivarium from the Instituto de Estudios de la Inmunidad Humoral (IDEHU). They received water and food ad libitum.

The following inoculations were performed by the oral route:

(i) Vehicle: 200 µl NaHCO3 buffer (1M, pH8).
(ii) 100 µg BODIPY FL Casein with 100 µg Omp19S.
(iii) 100 µg BODIPY FL Casein with 100 µg aprotinin.
(iv) BODIPY FL Casein.

After 15 min. from inoculation, mice were sacrificed by cervical dislocation, and stomachs were extracted and processed.

Stomachs extracts supernatants obtained were transferred to 96-well black/opaque plates (low autofluorescence) (Costar). Fluorescence emission was performed in a Victor3, Perkin Elmer, Waltham, Mass. plate reader.

The invention claimed is:

1. A composition comprising a non-lipidated bacterial outer-membrane polypeptide (Omp19S) of the *Brucella* genus as depicted in SEQ ID NO: 1 and at least an antigen selected from the group of allergens, viral antigens, bacterial antigens, parasitic antigens, fungal antigens and tumor cell antigens.

2. The composition according to claim 1, wherein the antigen is a mucosal antigen.

3. The composition according to claim 1, wherein the vaccine is selected from the group consisting of mucosal and parenteral vaccines.

* * * * *

SEQUENCE LISTING

<160> NUMBER OF SEQ ID NOS: 12

<210> SEQ ID NO 1
<211> LENGTH: 157
<212> TYPE: PRT
<213> ORGANISM: Brucella abortus

<400> SEQUENCE: 1

Met Gln Ser Ser Arg Leu Gly Asn Leu Asp Asn Val Ser Pro Pro Pro
1               5                   10                  15

Pro Pro Ala Pro Val Asn Ala Val Pro Ala Gly Thr Val Gln Lys Gly
            20                  25                  30

Asn Leu Asp Ser Pro Thr Gln Phe Pro Asn Ala Pro Ser Thr Asp Met
        35                  40                  45

Ser Ala Gln Ser Gly Thr Gln Val Ala Ser Leu Pro Pro Ala Ser Ala
    50                  55                  60

Pro Asp Leu Thr Pro Gly Ala Val Ala Gly Val Trp Asn Ala Ser Leu
65                  70                  75                  80

Gly Gly Gln Ser Cys Lys Ile Ala Thr Pro Gln Thr Lys Tyr Gly Gln
                85                  90                  95

Gly Tyr Arg Ala Gly Pro Leu Arg Cys Pro Gly Glu Leu Ala Asn Leu
            100                 105                 110

Ala Ser Trp Ala Val Asn Gly Lys Gln Leu Val Leu Tyr Asp Ala Asn
        115                 120                 125

Gly Gly Thr Val Ala Ser Leu Tyr Ser Ser Gly Gln Gly Arg Phe Asp
    130                 135                 140

Gly Gln Thr Thr Gly Gly Gln Ala Val Thr Leu Ser Arg
145                 150                 155

<210> SEQ ID NO 2
<211> LENGTH: 144
<212> TYPE: PRT
<213> ORGANISM: Brucella abortus

<400> SEQUENCE: 2

Met Ala Ser Lys Lys Asn Leu Pro Asn Asn Ala Gly Asp Leu Gly Leu
1               5                   10                  15

Gly Ala Gly Ala Ala Thr Pro Gly Ser Ser Gln Asp Phe Thr Val Asn
            20                  25                  30

Val Gly Asp Arg Ile Phe Phe Asp Leu Asp Ser Ser Leu Ile Arg Ala
        35                  40                  45

Asp Ala Gln Gln Thr Leu Ser Lys Gln Ala Gln Trp Leu Gln Arg Tyr
    50                  55                  60

Pro Gln Tyr Ser Ile Thr Ile Glu Gly His Ala Asp Glu Arg Gly Thr
65                  70                  75                  80

Arg Glu Tyr Asn Leu Ala Leu Gly Gln Arg Arg Ala Ala Thr Arg
                85                  90                  95

Asp Phe Leu Ala Ser Arg Gly Val Pro Thr Asn Arg Met Arg Thr Ile
            100                 105                 110

Ser Tyr Gly Asn Glu Arg Pro Val Ala Val Cys Asp Ala Asp Thr Cys
        115                 120                 125

Trp Ser Gln Asn Arg Arg Ala Val Thr Val Leu Asn Gly Ala Gly Arg
    130                 135                 140

<210> SEQ ID NO 3
<211> LENGTH: 22
<212> TYPE: DNA

```
<213> ORGANISM: Artificial Sequence
<220> FEATURE:
<223> OTHER INFORMATION: sense primer Omp19

<400> SEQUENCE: 3
ctggccatat gcagagctcc cg                                                22

<210> SEQ ID NO 4
<211> LENGTH: 24
<212> TYPE: DNA
<213> ORGANISM: Artificial Sequence
<220> FEATURE:
<223> OTHER INFORMATION: antisense primer Omp19

<400> SEQUENCE: 4
aaactcgagg cgcgacagcg tcac                                              24

<210> SEQ ID NO 5
<211> LENGTH: 22
<212> TYPE: DNA
<213> ORGANISM: Artificial Sequence
<220> FEATURE:
<223> OTHER INFORMATION: sense primer Omp16

<400> SEQUENCE: 5
gttgccatat ggcgtcaaag aa                                                22

<210> SEQ ID NO 6
<211> LENGTH: 24
<212> TYPE: DNA
<213> ORGANISM: Artificial Sequence
<220> FEATURE:
<223> OTHER INFORMATION: antisense primer Omp16

<400> SEQUENCE: 6
ttgccgctcg agccgtccgg cccc                                              24

<210> SEQ ID NO 7
<211> LENGTH: 29
<212> TYPE: DNA
<213> ORGANISM: Artificial Sequence
<220> FEATURE:
<223> OTHER INFORMATION: sense primer for eukaryote cloning Omp16

<400> SEQUENCE: 7
ctcctcgaga ccaccatggc gtcaaagaa                                         29

<210> SEQ ID NO 8
<211> LENGTH: 29
<212> TYPE: DNA
<213> ORGANISM: Artificial Sequence
<220> FEATURE:
<223> OTHER INFORMATION: antisense primer for eukaryote cloning Omp16

<400> SEQUENCE: 8
ttgtctagat taccgtccgg ccccgttga                                         29

<210> SEQ ID NO 9
<211> LENGTH: 30
<212> TYPE: DNA
<213> ORGANISM: Artificial Sequence
<220> FEATURE:
<223> OTHER INFORMATION: sense primer for eukaryote cloning Omp19

<400> SEQUENCE: 9
ggcattctcg agaccaccat gcagagctcc                                        30
```

```
<210> SEQ ID NO 10
<211> LENGTH: 27
<212> TYPE: DNA
<213> ORGANISM: Artificial Sequence
<220> FEATURE:
<223> OTHER INFORMATION: antisense primer for eukaryote cloning Omp19

<400> SEQUENCE: 10
ttttctagat cagcgcgaca gcgtcac                                         27

<210> SEQ ID NO 11
<211> LENGTH: 8
<212> TYPE: PRT
<213> ORGANISM: Artificial Sequence
<220> FEATURE:
<223> OTHER INFORMATION: OVA257-264 peptide

<400> SEQUENCE: 11

Ser Ile Ile Asn Phe Glu Lys Leu
1               5

<210> SEQ ID NO 12
<211> LENGTH: 17
<212> TYPE: PRT
<213> ORGANISM: Artificial Sequence
<220> FEATURE:
<223> OTHER INFORMATION: OVA323-339 peptide

<400> SEQUENCE: 12

Ile Ser Gln Ala Val His Ala Ala His Ala Glu Ile Asn Glu Ala Gly
1               5                   10                  15

Arg
```